US007252842B2

(12) United States Patent
Albayrak

(10) Patent No.: US 7,252,842 B2
(45) Date of Patent: *Aug. 7, 2007

(54) INDUCED PHASE TRANSITION METHOD FOR THE PRODUCTION OF MICROPARTICLES CONTAINING HYDROPHILIC ACTIVE AGENTS

(75) Inventor: Celal Albayrak, Munich (DE)

(73) Assignee: Alrise Biosystems GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/028,258

(22) Filed: Dec. 19, 2001

(65) Prior Publication Data

US 2003/0068381 A1 Apr. 10, 2003

Related U.S. Application Data

(60) Provisional application No. 60/300,021, filed on Jun. 21, 2001, provisional application No. 60/257,527, filed on Dec. 21, 2000.

(51) Int. Cl.
*A61K 9/16* (2006.01)
*A61K 9/14* (2006.01)

(52) U.S. Cl. ............... 424/494; 514/489; 514/490; 514/493; 514/499

(58) Field of Classification Search ........... 424/489, 424/490, 493, 494, 499
See application file for complete search history.

(56) References Cited

U.S. PATENT DOCUMENTS

| 3,523,906 A | 8/1970 | Vrancken et al. |
| 3,691,090 A | 9/1972 | Kitajima et al. |
| 3,737,337 A | 6/1973 | Schnoring et al. |
| 3,891,570 A | 6/1975 | Fukushim et al. |
| 3,943,063 A | 3/1976 | Morishita et al. |
| 3,960,757 A | 6/1976 | Morishita et al. |
| 4,166,800 A | 9/1979 | Fong |
| 4,384,975 A | 5/1983 | Fong |
| 4,389,330 A | 6/1983 | Tice et al. |
| 4,568,559 A | 2/1986 | Nuwayser et al. |
| 4,652,441 A | 3/1987 | Okada et al. |
| 4,675,189 A | 6/1987 | Kent et al. |
| 4,732,763 A | 3/1988 | Beck et al. |
| 4,835,139 A | 5/1989 | Tice et al. |
| 4,897,268 A | 1/1990 | Tice et al. |
| 4,917,893 A | 4/1990 | Okada et al. |
| 4,954,298 A | 9/1990 | Yamamoto et al. |
| 4,962,091 A | 10/1990 | Eppstein et al. |

(Continued)

FOREIGN PATENT DOCUMENTS

CA 2009941 8/1990

(Continued)

OTHER PUBLICATIONS

C. Albayrak, "Novel Methods for Engineering of Drug Loaded Nano and Microparticles of Uniform Morphology," Proceedings-28th Interl. Symp. on Cntrl. Rel. of Bioactive Mrtls. and 4th Consumer & Diversified Prod. Conf. San Diego, CA, US, Jun. 23-27, 2001, vol. 1, 846-847 Pub.: Cntrl. Rel. Soc., XP002211721.

(Continued)

*Primary Examiner*—Shengjun Wang
(74) *Attorney, Agent, or Firm*—Kagan Binder, PLLC

(57) ABSTRACT

Microparticles and a method for their production is described. The process of the present invention provides a simple, quick, and efficient one-pot process for the production of microparticles containing a hydrophilic active agent of various and uniform morphologies, including microcapsules, microspheres, and microsponges. The microparticles are preferably used for pharmaceutical applications.

28 Claims, 10 Drawing Sheets

Schematic of Induced Phase Transition Method

U.S. PATENT DOCUMENTS

| | | | |
|---|---|---|---|
| 4,994,281 A | 2/1991 | Muranishi et al. | |
| 5,019,400 A | 5/1991 | Gombotz et al. | |
| 5,271,961 A | 12/1993 | Mathiowitz et al. | |
| 5,330,767 A | 7/1994 | Yamamoto et al. | |
| 5,366,734 A | 11/1994 | Hutchinson | |
| 5,384,133 A | 1/1995 | Boyes et al. | |
| 5,445,832 A | 8/1995 | Orsolini et al. | |
| 5,500,161 A | 3/1996 | Andrianov et al. | |
| 5,503,851 A | 4/1996 | Mank et al. | |
| 5,536,508 A | 7/1996 | Canal et al. | |
| 5,556,642 A | 9/1996 | Kobayashi et al. | |
| 5,594,091 A | 1/1997 | Igari et al. | |
| 5,603,960 A | 2/1997 | O'Hagen et al. | |
| 5,609,886 A | 3/1997 | Wantier et al. | |
| 5,611,971 A | 3/1997 | Maedera et al. | |
| 5,622,657 A | 4/1997 | Takada et al. | |
| 5,631,020 A | 5/1997 | Okada et al. | |
| 5,631,021 A | 5/1997 | Okada et al. | |
| 5,635,216 A | 6/1997 | Thompson | |
| 5,643,605 A | 7/1997 | Cleland et al. | |
| 5,648,095 A | 7/1997 | Illum et al. | |
| 5,648,096 A | 7/1997 | Gander et al. | |
| 5,650,173 A | 7/1997 | Ramstack et al. | |
| 5,661,125 A | 8/1997 | Strickland | |
| 5,676,968 A | 10/1997 | Lipp et al. | |
| 5,700,486 A | 12/1997 | Canal et al. | |
| 5,723,269 A | 3/1998 | Akagi et al. | |
| 5,733,567 A | 3/1998 | Arola et al. | |
| 5,766,637 A | 6/1998 | Shine et al. | |
| 5,783,567 A | 7/1998 | Hedley et al. | |
| 5,792,477 A | 8/1998 | Rickey et al. | |
| 5,851,451 A | 12/1998 | Takechi et al. | |
| 5,853,698 A | 12/1998 | Straub et al. | |
| 5,863,554 A | 1/1999 | Illum et al. | |
| 5,902,565 A | 5/1999 | Cox et al. | |
| 5,902,834 A | 5/1999 | Porrvik et al. | |
| 5,916,598 A | 6/1999 | Rickey et al. | |
| 5,922,357 A | 7/1999 | Coombes et al. | |
| 5,929,196 A | 7/1999 | Kissel et al. | |
| 5,955,143 A | 9/1999 | Wheatley et al. | |
| 5,980,947 A | 11/1999 | Yamakawa et al. | |
| 5,981,474 A | 11/1999 | Manning et al. | |
| 5,985,312 A | 11/1999 | Jacob et al. | |
| 5,993,855 A | 11/1999 | Yoshimoto et al. | |
| 6,007,845 A | 12/1999 | Domb et al. | |
| 6,020,004 A | 2/2000 | Shah | |
| 6,048,551 A | 4/2000 | Hilfinger et al. | |
| 6,080,429 A | 6/2000 | Cleland et al. | |
| 6,110,503 A | 8/2000 | Rickey et al. | |
| 6,113,943 A | 9/2000 | Okada et al. | |
| 6,120,805 A | 9/2000 | Spenlehauer et al. | |
| 6,143,211 A | 11/2000 | Mathiowitz et al. | |
| 6,290,983 B1 | 9/2001 | Rickey et al. | |
| 6,291,013 B1 | 9/2001 | Gibson et al. | |
| 6,294,204 B1 * | 9/2001 | Rossling et al. | 424/497 |
| 6,410,056 B1 * | 6/2002 | Setterstrom et al. | 424/501 |
| 6,899,898 B2 * | 5/2005 | Albayrak | 424/489 |

FOREIGN PATENT DOCUMENTS

| | | |
|---|---|---|
| CA | 2100925 | 1/1994 |
| DE | 19916384 | 10/2000 |
| EP | 202065 | 5/1986 |
| EP | 251476 | 5/1986 |
| EP | 190833 | 8/1986 |
| EP | 302582 | 3/1987 |
| EP | 330180 | 2/1989 |
| EP | 0315875 | 5/1989 |
| EP | 438426 | 9/1989 |
| EP | 580428 | 7/1993 |
| EP | 582459 | 8/1993 |
| EP | 797615 | 3/1995 |
| EP | 04481732 | 3/1995 |
| EP | 0668073 | 4/1999 |
| FR | 2797784 | 3/2001 |
| GB | 1405108 | 12/1971 |
| GB | 2234896 | 2/1991 |
| WO | WO 90/13780 | 11/1990 |
| WO | WO 97/19676 | 6/1997 |
| WO | WO 98/07442 | 2/1998 |
| WO | WO 98/27962 | 7/1998 |
| WO | WO 99/20253 | 4/1999 |
| WO | WO 99/29304 | 6/1999 |
| WO | WO 99/58112 | 11/1999 |
| WO | WO 99/59548 | 11/1999 |
| WO | WO 00/04916 | 2/2000 |
| WO | WO 00/28969 | 5/2000 |
| WO | WO 01/28591 | 4/2001 |

OTHER PUBLICATIONS

Arshady, "Preparation of biodegradable microspheres and microcapsules: 2. Polyactides and related polyesters," J. of Cont. Rel., 17th ed., p. 1-22, (Feb. 5, 1991).

Watts et al., "Microencapsulation Using Emulsification/Solvent Evaporation: An Overview of Techniques and Applications," Critical Reviews in Therapeutic Drug Carrier Systems, vol. 7 (No. 3), p. 235-259, (Feb. 5, 1990).

Wang et al., "Preparation and Characterization of Poly(lactic-co-glycolic acid) Microspheres for Targeted Delivery of a Novel Anticancer Agent, Taxol," Chem. Pharm. Bull., Pharmaceutical Society of Japan, vol. 44 (No. 10), p. 1935-1940, (Oct. 1, 1996).

Ghaderi et al., "Effect of preparative parameters on the characteristics of poly(D.L-lactide-co-glycolide) microspheres made by the double emulsion method," International Journal of Pharmaceutics, Elsevier Science B.V., p. 205-216, (Jun. 16, 1996).

Cleland, "Solvent evaporation processes for the production of Controlled Release Biodegradable Microsphere Formulations for Therapeutics and Vaccines," Biotechnol. Prog., 1st ed., American Chemical Society & American Institute of Chemical Engineers, vol. 14 (No. 1), p. 102-107, (Feb. 6, 1998).

O'Donnell et al., "Properties of multiphase microspheres of poly(dl-lactic acid) or poly(dl-lactic-co-glycolic acid) produced by mechanical agitation, sonication, or potentiometric dispersion," J. Microencapsulation, Taylor & Francis Ltd., vol. 13 (No. 6), p. 667-677, (Feb. 5, 1996).

Carti, "A new approach to imporved stability and controlled release in double emulsions, by the use of graft-comb polymeric amphiphiles," Acta Polym, Wiley-VCH (Weinhelm), p. 606-616, (Feb. 5, 1998).

Aftabroushad et al., "Factors Influencing the Entrapment of a Water Soluble Model Drug into Injectable Microparticles Prepared Using Solvent Evaporation and Phase Seperation Techniques," Eur. J. Pharm BioPharm, medpharm GmbH Scientific Publishers (Stuttgart), vol. 40 (No. 4), p. 237-242, (Feb. 5, 1994).

Abstract of EP0315875, Schmiedel et al, (May 17, 1989), 1 pg.

US 5,849,884, 12/1998, Woiszwillo et al. (withdrawn)

* cited by examiner

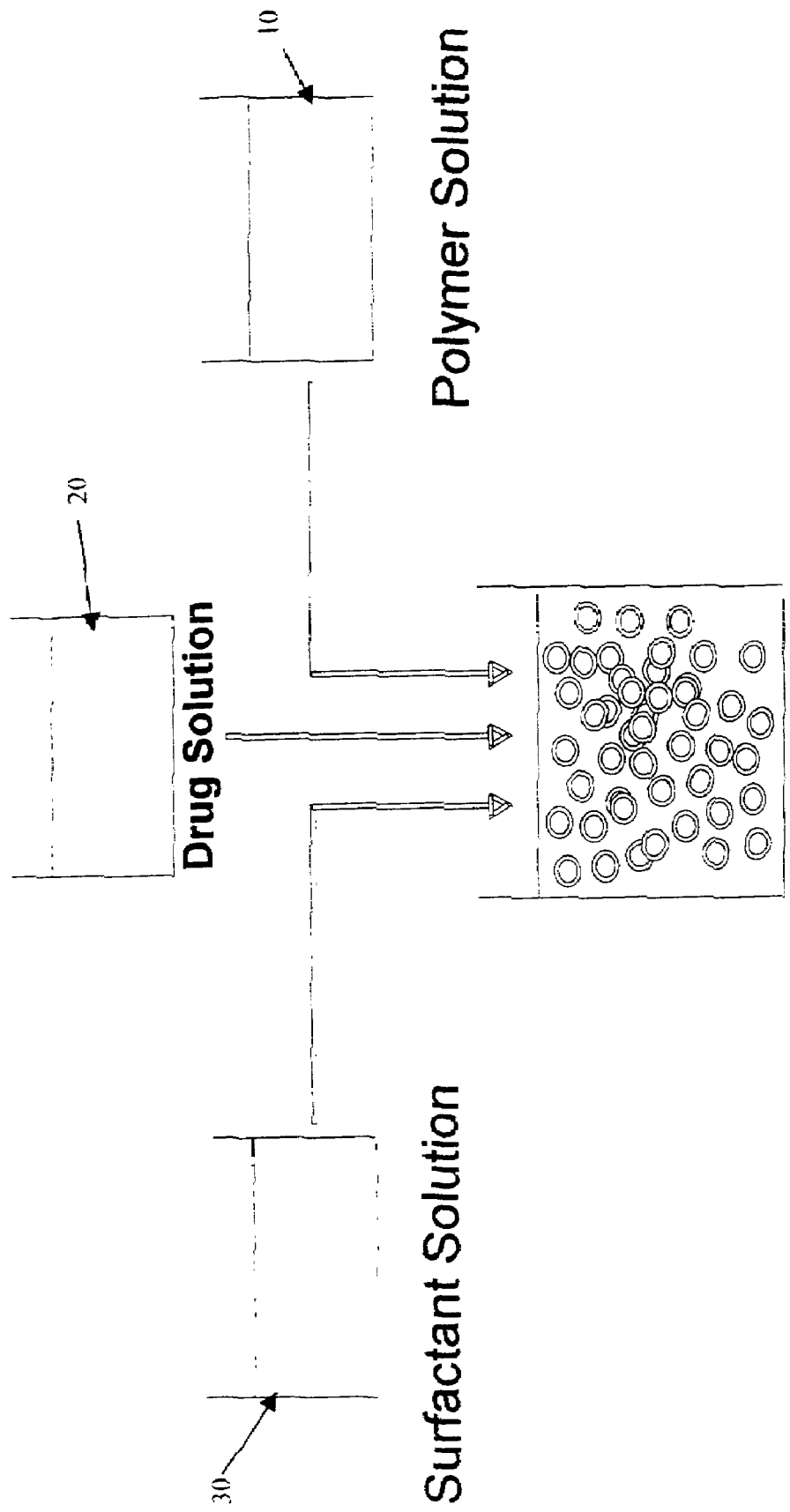

Electron Microscopic Pictures of Microscapsules

Light Microscopic Pictures

Microcapsules

Light Microscopic Pictures

Microsponges

Light Microscopic Pictures
Microsponges

Electron Microscopic Pictures
Microsponges

Electron Microscopic Pictures

Microspheres

INDUCED PHASE TRANSITION METHOD FOR THE PRODUCTION OF MICROPARTICLES CONTAINING HYDROPHILIC ACTIVE AGENTS

FIELD OF THE INVENTION

This invention is directed to a process for the production of microparticles containing a water-soluble biologically active agent including peptides, proteins, DNA plasmids, or other active agent, as well as the microparticles produced by this process. Microparticles of varying morphologies can be produced, such as microcapsules, microspheres, and microsponges. According to the invention, a simplified one-pot process for producing such microparticles is provided.

BACKGROUND OF THE INVENTION

There are numerous bioengineered peptide and protein drugs currently on the market or undergoing clinical trials, including hormones, growth factors, cytokines, monoclonal antibodies, and proteins to block infectious diseases. Their efficacy, however, is strongly restricted and their bioavailability strongly compromised during oral administration because of their sensitivity to hydrolysis in the acid environment of the stomach and by enzymatic degradation. Proteins are large molecules that cannot be administered orally because of enzymatic breakdown and are, for the most part, too large to be delivered efficiently by a transdermal patch. They also suffer from the fact that they are relatively unstable and have short half-lives in vivo. These difficulties have required protein drugs to be given either by constant infusion or frequent injection, forms of administration that limit their acceptability by physicians and patients.

Appropriate formulations that avoid the above-mentioned problems include depot systems in the form of polymer microparticles which are also widely known for peptides and proteins and are described in the literature. These depot systems possess the advantage that they protect peptides, proteins and other biologically active substances from rapid deactivation and, because of this, preserve their pharmacological efficacy and thus permit administration in low doses. Additional advantages of these formulations include a reduction in undesired side effects, due to the ability to provide lower doses; reduction in the total number of administrations; and the potential for controlled as well as targeted release of the active agents.

Known methods for micro- or nanoencapsulation of active agents including peptides and proteins can be summarized as follows:

I. Solvent Evaporation

Solvent evaporation involves the dissolving of the polymer in an organic solvent which contains either dissolved or dispersed active agent. The polymer/active agent mixture is then added to an agitated continuous phase which is typically aqueous. Emulsifiers are included in the aqueous phase to stabilize the oil-in-water emulsion. The organic solvent is then evaporated over a period of several hours or more, thereby depositing the polymer around the core material. The solvent evaporation procedure is disclosed in U.S. Pat. No. 4,389,330.

However, the solvent evaporation technique is often not preferred because active ingredient is often lost during the solvent extraction process. This is because the process involves emulsification into an aqueous phase, and a water soluble drug will often rapidly partition from the more hydrophobic polymer-solution phase into the aqueous surroundings.

Encapsulation by the solvent evaporation process also leads to the production of microspheres. The active ingredient to be encapsulated is traditionally dispersed in a solution of polymer in a volatile organic solvent. This phase is emulsified by means of a surface-active agent in a non-miscible dispersing medium (water or mineral oil). The organic solvent evaporates with stirring. After the evaporation, the microspheres are recovered by filtration or centrifugation.

The advantages of the technique are the absence of toxic solvents such as heptane, and the absence of agglomeration of the microspheres. Solvent evaporation is simpler, more flexible and easier to industrialize than other processes such as phase separation or coacervation, and it makes it possible to use reduced amounts of solvent.

Traditionally, solvent evaporation is primarily applied to the encapsulation of lipophilic substances such as steroids and nitrosoureas. The microencapsulation of hydrophilic active ingredients requires the use of an apolar dispersing phase such as a mineral oil. Acetone/paraffin systems are conventionally used. However, the levels of incorporation of the hydrophilic active ingredient into the microspheres relative to the amounts employed in the process are fairly low and, moreover, this system involves a limitation with respect to the types of polymers which may be used given that it requires the polymer to be soluble in acetone, which is the case with lactic acid polymers, but which is not the case for lactic acid and glycolic acid copolymers. The technique by emulsion/evaporation is therefore traditionally recognized as unsuitable for water-soluble peptides and for all water-soluble substances.

Microparticles produced according to the solvent evaporation method are described in two Canadian Patent Applications, CA 2,100,925 (Rhone-Merieux) and CA 2,099,941 (Tanabe Seiyaku Co.).

According to CA 2,099.941, the water-soluble active ingredient and the biodegradable polymer are initially dissolved in a solvent or a solvent mixture. The solvent/solvent mixture is then eliminated and the formed solid dispersion dissolved in another organic solvent immiscible with water. The resulting solution (oil phase) is emulsified in an aqueous phase so that a W/O emulsion is formed. The organic solvent of the oil phase is finally evaporated. Specific examples cited in the patent describe the use of poly-(lactide-co-glycolide) polymer (PLGA) as matrix and thyreotropin releasing hormone (TRH) or one of its derivatives as active principal.

The components are initially dissolved in a mixture of acetonitrile/ethanol and optionally water, or only acetonitrile, or in a mixture consisting of acetonitrile and aqueous gelatin or dichloromethane and ethanol.

Organic solvents, like dichloromethane or chloroform, are used to dissolve the forming solid dispersion. An aqueous polyvinyl alcohol solution represents the aqueous phase. The size of the microparticles lies at a diameter from 1 to 100 μm and, according to the specific examples, at about 50 μm to ≦100 μm.

According to CA 2,100,925, microparticles of LHRH hormone and analogs are produced by dispersal of the powdered LHRH hormone in two organic solvents, the one solvent (dispersion solvent) permitting production of a homogeneous suspension by simple agitation. The second solvent is readily miscible with water and therefore makes microdispersion of the organic phase in the aqueous phase possible. Dichloromethane or, as an alternative, chloroform is used as second solvent. The microparticles have a diameter from 1–250 μm. The microparticles are preferably larger than 50–60 μm.

The morphology of the microparticles so produced is again very nonhomogeneous. As already mentioned above, the employed halogenated solvents are also toxicologically objectionable. This method also requires large amounts of surfactants.

II. Phase Separation

Another technique which can be used to form microparticles is phase separation, which involves the formation of a water-in-oil emulsion or oil in water emulsion. The polymer is precipitated from the continuous phase onto the active agent by a change in temperature, pH, ionic strength or the addition of precipitants. Again, this process suffers primarily from loss of active ingredient due to denaturation.

Consequently, the use of phase separation for production of microparticles may be better suited for the formulation of microparticles containing more water soluble compounds, particularly water-soluble polypeptides. Phase separation methods of microparticle preparation allow a more efficient incorporation of drugs and can easily be scaled up for industrial purposes. The process of phase separation usually employs an emulsion or a suspension of the drug particles in a solution of a high molecular weight polymer and an organic polymer solvent. A non-solvent is then added to the suspension or emulsion, causing the polymer to separate from solution and to encapsulate the suspended drug particles or droplets containing them. The resulting microparticles (which are still swollen with solvent) are then normally hardened by a further addition of a non-solvent or by some other process which strengthens and improves the properties of the microparticles.

First, the product to be encapsulated is dispersed in the solution of a polymer intended to subsequently form the matrix of the microcapsules. Secondly, the coacervation of the polymer is induced by a physico-chemical modification of the reaction medium, in particular by means of a phase separation inducing agent. Thirdly, coacervate droplets that form around the material to be encapsulated are stabilized and solidified by means of a nonsolvent of the polymer, for example heptane.

Pharmaceutical formulations of water-soluble peptides and proteins in microcapsule form that were produced based on coacervation and emulsion phase separation are known from U.S. Pat. Nos. 4,675,189, 4,675,800, 4,835,139, 4,732, 763, and 4,897,268; U.K. Patent Application No. 2,234,896; and EP 330,180 and EP 0 302 582 and by Ruiz et al. in the international Journal of Pharmaceutics (1989) 49:69–77 and in Pharmaceutical Research (1990) 9:928–934.

Methods are described in these disclosures in which the employed copolymer, preferably poly-(lactide-co-glycolide) polymer, is dissolved in a halogenated organic solvent, preferably dichloromethane, and an aqueous peptide solution dispersed in this polymer solution. A so-called coacervation agent is then added. The coacervation agent is soluble in the employed organic solvent, but the polymer is not, so that precipitation of the polymer occurs with incorporation of the dispersed polypeptides.

Silicone oil is ordinarily used as coacervation agent for phase separation. After addition of silicone oil, a large amount of heptane must also be added, which produces curing of the microcapsules. The encapsulation efficiency of this method is about 70% (U.S. Pat. No. 4,835,139). The microcapsules so produced have a diameter of 1–500 μm, according to the examples preferably 10–50 μm.

The main disadvantage of this method is the use of large amounts of solvents with, in addition to cost constraints, problems of toxicity linked to the solvents, such as heptane, used. This is because the techniques by coacervation using heptane do not enable its complete removal. A large amount of residual solvents, of the order of 5 to 10% of heptane, is observed in the microspheres.

Independently of the above, it has also been observed that aggregates of microspheres causing a high loss of yield in the production of these microspheres by this method and sometimes requiring the total rejection of some batches which have thus become unusable, were often produced. The tendency of the microspheres to aggregate causes additional difficulties at the time of suspending the microspheres for injection, in the case of injectable microspheres.

Another disadvantage of the technique by phase separation is the nonhomogeneous distribution of the active substance in the microspheres with irregular release, and in general a first phase of accelerated release ("burst effect"). This is observed in particular when the active substance is suspended in the polymer solution, in particular because it is not soluble in the solvent for the polymer. This generally applies, for example, to polypeptides. Additionally, problems include the formation of non-spherical particles, formation of particles that are not smooth and have defects, the presence of large particles with a wide range of sizes, and the presence of non-particulate material.

III. Double Emulsion

Another example of a process to form microparticles is shown in U.S. Pat. No. 3,523,906. In this process a material to be encapsulated is emulsified in a solution of a polymeric material in a solvent which is immiscible with water and then the emulsion is emulsified in an aqueous solution containing a hydrophilic colloid. Solvent removal from the microcapsules is then accomplished in a single step by evaporation and the product is obtained.

The double emulsion (W/O/W) and solvent evaporation method, is also disclosed in Patent U.S. Pat. No. 3,523,906 is for technical applications, and employs non-biodegradable polymers as wall material (for example, polystyrene), which are dissolved in halogenated hydrocarbons (dichloromethane or chloroform).

Patent U.S. Pat. No. 5,330,767 describes the use of the W/O/W double emulsion and solvent evaporation method disclosed in U.S. Pat. No. 3,523,906 for pharmaceutical purposes. In contrast to the method described in U.S. Pat. No. 3,523,906, only biodegradable polymers are used here. Other double emulsion process for microencapsulation are disclosed in EP 190,833 and WO 99/58112, and U.S. Pat. Nos. 5,648,095, 5,902,834, 4,954,298, 5,841,451, 4,917,893 and 4,652,441.

A serious shortcoming of these methods, however, is that the microparticles so produced consist of a mixture of monolithic microspheres, microcapsulesand microsponges. In addition to the limited encapsulation efficiency (30–60%), the nonhomogeneous morphology of the microparticles has a significant effect on the release behavior of the product (R. Baker, Controlled Release of Biologically Active Agents, A Wiley-Interscience Publications, 1987). This simultaneously also hampers reproducibility of product quality.

Moreover, the process involves a complex multistep process, in which the specific effect of individual process steps on product quality is uncertain, for which reason process optimization is also difficult. The process is very time-intensive and requires large volumes of surfactant solutions.

Another shortcoming of the process is the use of solvents with high toxicological potential (Henschler D., Angew. Chem. 106 (1994), 1997–2012).

IV. Spray Drying

Another method for production of biodegradable microparticles, in which water-soluble peptides and proteins can be incorporated, described in EP 0 315 875 (Hoechst AG), is based on the spray-drying process. In this process, an aqueous peptide or protein solution is emulsified in an organic polymer solution and this emulsion is then spray-dried. Examples of other spray drying processes are disclosed in U.S. Pat. Nos. 5,648,096, 5,723,269, and 5,622,657.

A mixture of polyhydroxybuteric acid and poly(lactide co-glycolide) polymer in a mixing ratio between 99:1 and 20:80 is used as biodegradable polymer. The peptide/protein is then in micronized form or in aqueous solution. Chloroform, dichloromethane, DMF or a solvent mixture of water/ethanol/chloroform are considered as solvent. Chloroform is used in the mentioned examples. Spray-drying preferably occurs at temperatures from 45° C. to 95° C.

Shortcomings of this method include the low yield (45% of the theoretically possible) and the high initial burst effect. In addition, use of solvents, like dichloromethane and chloroform, leads to toxicologically objectionable residual solvent contamination in the end product. Spray-dried microparticles, in principle, also exhibit a strong tendency toward agglomeration, and agglomerates with a diameter of up to 100 µm often form.

In spray drying the polymer and the drug are mixed together in a solvent for the polymer. The solvent is then evaporated by spraying the solution into a drying chamber which is also provided with a source of a drying agent. This results in polymeric droplets containing the drug. However, sensitive substances such as proteins can be inactivated during the process due to the elevated temperatures used and the exposure to organic solvent/air interfaces. Further disadvantages include generation of high porosity due to rapid removal of the organic solvent. A variation that has been introduced to avoid these shortcomings is the use of low temperature during microsphere formation (U.S. Pat. No. 5,019,400, WO 90/13780 and U.S. Pat. No. 4,166,800). Microcapsules have been prepared using spray coating of drug-containing microparticles with PLGA polymers as described in U.S. Pat. No. 4,568,559.

Other examples of microencapsulation methods are known in the prior art. For example, another example of a conventional prior art microencapsulation process is shown in U.S. Pat. No. 3,737,337 wherein a solution of a wall or shell forming polymeric material in a solvent is prepared. The solvent is only partially soluble in water. A solid or core material is dissolved or dispersed in the polymer containing solution and thereafter in a single step, the core material containing solution is dispersed in an aqueous liquid which is immiscible with the organic solvent in order to remove solvent from the microcapsules. In still another process as shown in U.S. Pat. No. 3,691,090 organic solvent is evaporated from a dispersion of microcapsules in an aqueous medium in a single step, preferably under reduced pressure. Similarly, the disclosure of U.S. Pat. No. 3,891,570 shows a method in which solvent from a dispersion of microcapsules in polyhydric alcohol medium is evaporated from the microcapsules by the application of heat or by bringing the microcapsules under reduced pressure. Another example of a one-step solvent removal process is shown in U.S. Pat. No. 3,960,757.

WO 97/19676 discloses a process for microencapsulation of hydrophilic active agents. An aqueous active agent solution having a pH of 6.0–8.0 is added to a polymer solution. An aqueous surfactant phase is then added to form microcapsules comprising an inner aqueous core containing the active agent.

WO 99/20253 discloses a process for forming microparticles wherein a drug emulsion or dispersion is injected into an aqueous polyethylene glycol (PEG) solution which acts as a continuous phase and as an extraction medium. The solvent for the emulsion or dispersion should be immiscible or essentially immiscible but slightly or very slightly soluble in the water/PEG solution. Examples include ethyl acetate, dichlormethane, methyl ethyl ketone and methyl isobutyl ketone alone or in combination. A high concentration of PEG is used to prevent diffusion of active agent from the droplets/particles. The process requires several hours of mixing to produce the microparticles.

Additional processes for producing microparticles are disclosed in U.S. Pat. Nos. 6,291,013, 5,792,477, 5,643,605, 5,922,357, 6,309,569 and in PCT publications WO 99/59548 and WO 01/28591. Whatever the process, the drug release pattern for a microparticle is dependent upon numerous factors. For example, the type of drug encapsulated and the form in which it is present (i.e. liquid or powder) may affect the drugs release pattern. Another factor which may affect the drug release pattern is the type of polymer used to encapsulate the drug. Other factors affecting the drug release pattern include the drug loading, the manner of distribution in the polymer, the particle size and the particle shape. Despite numerous modifications to the above processes to produce microparticles for pharmaceutical applications, problems remain which reduce the effectiveness and reproducibility of the microparticles produced by these methods, particularly for use in controlled release delivery systems.

DEFINITIONS

As used herein, the term "drug phase" refers to the polymer/active agent-containing phase formed during the manufacture of the microparticles according to the invention which results from the addition of an active agent to the organic polymer solution existing prior to the addition of the aqueous surfactant phase. The drug phase may be a solution, dispersion, suspension, or emulsion.

As used herein, the term "microcapsule" refers to a microparticle wherein a polymeric wall encases a core consisting of an aqueous solution or suspension. In the case of microcapsules encapsulating hydrophilic active agents, the core comprises an aqueous solution including the active agent.

As used herein, the term "microparticle" refers to substantially spherical particles having a mean diameter within about 20 nm to 1000 µm and includes microcapsules, microspheres, and microsponges.

As used herein, the term "microsphere" refers to a microparticle wherein an active agent is embedded within a solid polymeric matrix.

As used herein, the term "microsponge" refers to a microparticle wherein an active agent is embedded within a polymeric matrix comprising an open-cell structure.

As used herein, the term "surfactant phase" refers to an aqueous solution having a surfactant or mixture of surfactants dissolved therein with or without additional excipients.

As used herein, the term "volume fraction" refers to the volume of the referenced phase with respect to the entire volume of material used to produce the suspension of microparticles according to the invention. For example, the volume fraction of the aqueous surfactant phase is the volume of aqueous surfactant phase divided by the volume total of the drug phase and aqueous surfactant phase.

SUMMARY OF THE INVENTION

The present invention provides a novel, simple and mild process for the encapsulation of hydrophilic active agents in biodegradable polymers which avoids or reduces the disadvantages seen in the prior art. The process produces non-agglomerating, microparticles in the size range from 20 nm to 1,000 μm at encapsulation efficiencies of greater than 85%, preferably greater than 90% using toxicologically acceptable solvents. The process of the present invention employs a minimal volume of surfactant solution resulting in a reduced production time compared with other prior art processes. Additionally, the process according to the invention may be readily scaled up to meet commercial-scale production needs as it provides a much simplified, one-pot process compared to processes of the prior art.

Additionally, the process according to the present invention provides greater control over particle size distributions, allows for the production of microparticles having a desired, as well as more uniform morphology, and enables a reduction of the mixing energy required to obtain the microparticles. Further, the present invention provides that a smaller amount of surfactant solution is necessary to form the microparticle suspension compared to prior art processes wherein the drug phase is typically injected into a large excess of surfactant solution. This greatly reduces processing time and minimizes the amount of surfactant which, in some cases, needs to be removed from the microparticles prior to their intended use.

More specifically, the present invention relates to a process of encapsulating a hydrophilic active agent in a biodegradable polymer comprising dissolving a polymer in a halogen-free solvent that is at least partially water-miscible to form a polymer solution; adding an active agent to the polymer solution to form a drug phase contained in a vessel; adding a predetermined amount of an aqueous surfactant phase to the vessel containing the drug phase with mixing, said predetermined amount being sufficient to provide that the surfactant phase becomes the continuous phase and extraction medium in order to extract an amount of the solvent from the drug phase such that a suspension of microparticles is produced upon addition of the surfactant phase to the drug phase without requiring removal of the solvent from the vessel.

BRIEF DESCRIPTION OF THE DRAWINGS

FIG. 1 depicts a schematic of the process according to one aspect of the invention.

DETAILED DESCRIPTION OF THE INVENTION

Figure 2B:
FIGS. 2a and 2b depict electron microscopic images of microcapsules produced in Example 1.

It has surprisingly been found that by the appropriate selection and addition of an aqueous surfactant phase to a drug phase which comprises an organic solvent or solvent mixture that is at least partially water-miscible and preferably has a water solubility of about 1.5–40 wt %, the aqueous surfactant phase acts as both the continuous phase and extraction medium, thereby allowing a suspension of microparticles to almost immediately form without requiring solvent evaporation or other such solvent removal step. The process of the present invention can be practiced to prepare microparticles of various morphologies including microcapsules, microsponges, microspheres, and mixtures thereof and can be used to encapsulate hydrophilic active agents.

According to the present invention, the polymer for microencapsulation is dissolved in a halogen-free solvent or solvent mixture partially miscible with water to form an organic polymer solution. The solubility of the organic solvent or solvent mixture in water or in the aqueous surfactant phase, with or without buffers, has a value between 1.5% (w/w) and 40% (w/w). When using solvents with a water solubility greater than 40% w/w, it is used in admixture with a larger volume of another solvent of lower water solubility such that the water solubility of the solvent mixture is reduced to less than 40% w/w. A drug phase is then prepared depending on the active agent to be encapsulated and the desired microparticle morphology as described in detail below.

Once the drug phase is prepared, an aqueous surfactant phase is added to the vessel in which the drug phase is contained as detailed below. The polymer solvent is selected based on its miscibility in the aqueous surfactant phase. According to the present invention, the polymer solvent and aqueous surfactant solutions are selected based on their solubility parameters ($\delta(\text{cal/cm}^3)^{1/2}$). According to preferred embodiments, $\delta_{polymer\ solvent} - \delta_{aqueous\ phase} < 0$ preferably. $\delta_{polymer\ solvent} - \delta_{aqueous\ phase}$ is within the range 0 to $-15\delta(\text{cal/cm}^3)^{1/2}$.

In addition to the solubility parameters, the volume fractions of each of the solutions combined according to the process of the present invention are selected in order to provide that a suspension of microparticles is formed almost immediately upon combining the drug phase with the aqueous phase. Accordingly, the volume ratio of the polymer phase: surfactant phase is within the range of 1:2–1:30, preferably 1:2–1:20.

A suspension of microparticles is immediately formed, preferably within one minute of mixing. Further mixing is performed, preferably for up to about 30 minutes, and more preferably about 4–10 minutes. The microparticles can then be removed from the suspension by well known techniques. This surprisingly simple method for producing microparticles results in significant improvements over the prior art, including the use of less toxic polymer solvents, control over microparticle morphology, and a much simplified process with a dramatically reduced production time compared to prior art processes. Further, the present invention readily lends itself to scale-up for large scale production.

According to one embodiment directed to the encapsulation of hydrophilic active agents in microcapsules as depicted in FIG. 1, the drug phase is prepared by dissolving the hydrophilic active agent in water or in an aqueous buffer solution with a pH value between 2.0 and 11 to form aqueous active agent solution 20. Polymer solution 10 is prepared by dissolving polymer in an organic solvent, which is then added to vessel 40. Aqueous active agent solution 20 is added to the organic polymer solution in vessel 40 and dispersed by means of a mechanical agitator to form an intermediate drug phase comprising a W/O emulsion. It is worth noting that since the one-pot process of the present invention is a relatively fast process, a W/O emulsion at this point in the processing is never truly observed and thus is referred to as merely an intermediate W/O emulsion drug phase for the sake of this discussion. An aqueous surfactant phase 30 is then added to the drug phase in vessel 40 to produce a suspension of microparticles 50 in vessel 40 as discussed below.

To form the microparticle suspension, a defined volume of an aqueous solution or buffer solution containing a surfactant or surfactant mixture is added as continuous phase to the drug phase produced by homogenization during agitation, so that a phase transition from the organic phase to the aqueous phase occurs with immediate formation of a microparticle suspension. In a preferred embodiment, the volume of continuous aqueous surfactant phase required for the phase transition is roughly calculated under the assumption that the polymer microparticles in the continuous aqueous surfactant phase occupy the cavities in a "body centered cubic" or "face centered cubic" or "hexagonal close pack" arrangement. According to this preferred embodiment, the volume fraction of aqueous surfactant phase is greater than approximately 60%, preferably between 65 and 80%, and most preferably between 68% and 74%.

As discussed above, according to this embodiment directed to encapsulation of hydrophilic active agents in microcapsules, the addition of the aqueous surfactant phase to the drug phase results in the almost immediate formation of a microparticle suspension. The process according to the present invention eliminates the step of forming a double emulsion (W/O/W) from which solvent must be eliminated prior to formation of any microparticles as in the double emulsion processes mentioned above. As a result, the process of the present invention provides better control over particle size distributions and produces microparticles of smaller mean diameters and more uniform morphology and increased encapsulation efficiencies. Additionally, the microparticle suspension is formed within minutes of adding the aqueous surfactant phase to the drug phase, preferably within one minute as compared to prior art processes requiring production times of up to several hours.

Once the suspension of microparticles is formed, the solvent or solvent mixture is eliminated by the usual methods, preferably in vacuum and/or an air/nitrogen stream, or also by filtration or extraction. After removing the solvent, the microparticles are additionally subjected to "cross-flow" filtration if desired; as a result, they are mildly freed from surfactant residues and solvent residues as well as from any non-encapsulated active substance or, as the case may be, any active substance that is adhering to the surface.

The microparticles are concentrated after washing with water (centrifuging or filtration) and optionally freeze-dried or spray dried as described in the above-referenced patents, or dried in a fluidized bed as described for example in U.S. Pat. No. 6,080,429.

According to a preferred embodiment, a viscosity modifier is added to the aqueous surfactant phase. It has surprisingly been discovered that the replacement of a portion of the water of the aqueous surfactant phase with a viscosity modifying agent such as glycerol results in smaller mean microparticle diameters and smaller microparticle size distributions, as well as increases in drug loadings and encapsulation efficiency.

The viscosity of the aqueous surfactant phase can be varied over several orders of magnitude by the successive replacement of water by glycerin. According to this embodiment, the aqueous surfactant phase is provided with about 1–80 wt %, preferably 5–50 wt %, of a viscosity modifier such as glycerol. Other viscosity modifiers include polyethylene glycol, hyaluronic acid, cellulose polymers and derivatives of cellulose, chitosane and other bioadhesive polymers, and other agents known in the art such as those disclosed in U.S. Pat. Nos. 4,652,441, 4,711,282, 4,917,893, and 5,061,492, hereby incorporated in their entirety by reference.

According to another preferred embodiment, a co-solvent is added to the aqueous surfactant phase. The co-solvent is water miscible and is further characterized as being a solvent for the polymer solvent while not a solvent for the polymer. According to this embodiment, the aqueous surfactant phase is capable of extracting more of the polymer solvent from the organic polymer solution compared to an equivalent volume of aqueous surfactant phase absent any co-solvent. This reduces the volume fraction of aqueous surfactant phase required to form the microparticle suspension, thus reducing the amount of surfactant to be removed from the microparticle suspension. The amount of co-solvent to be added to the aqueous surfactant phase is primarily dependent upon the polymer and polymer solvent selected. Typically, about 1–40 wt % co-solvent is added to the aqueous surfactant phase according to this embodiment. Suitable co-solvents include, but are not limited to, alcohols such as ethanol, methanol, ethers, and polyethylene glycol.

According to another preferred embodiment, buffered solutions are used in order to increase encapsulation efficiencies. For example, a significant number of hydrophilic proteins and peptides are stable at a neutral pH of around 7.0. For encapsulation of such hydrophilic active agents in microcapsules, the active agent is dissolved in a buffered solution to maintain pH in which the active agent remains stable, typically around pH 4.0–9.0. The aqueous surfactant phase is likewise provided with a buffer in order to keep the pH of the aqueous surfactant phase at a range where the active agent is not soluble. Such selection of buffers acts to keep the active agent in the drug phase and prevents migration of the active into the aqueous surfactant phase extraction medium, thereby increasing the encapsulation efficiency of the active agent into the microcapsules. It is to be understood that such use of buffers can also be used to increase encapsulation efficiencies according to any of the other embodiments set forth above.

According to the present invention, the desired particle size can be adjusted via the stirring speed and the time of stirring and also via the surfactant concentration. The microspheres of the instant invention can be prepared in any desired size, ranging from about 0.1 μm to upwards of about 1000 μm in diameter, by varying process parameters such as stir speed, volume of solvent used in the phase transition step, temperature, concentration of polymer(s), and inherent viscosity of the polymer(s). Such selection criteria can be readily determined by one of ordinary skill in the art.

The present invention can be practiced to encapsulate a wide range of hydrophilic active agents, including proteins, peptides, polypeptides, oligonucleotides, plasmids or DNA. Examples of active agents suitable for use in this invention include but are not limited to calcitonin, erythropoietin (EPO), Factor VIII, Factor IX, ceredase, cerezyme, cyclosporin, granulocyte colony stimulating factor (GCSF), alpha-1 proteinase inhibitor, elcatonin, granulocyte macrophage colony stimulating factor (GMCSF), growth hormones including human growth hormone (HGH) and growth hormone releasing hormone (GHRH), heparin, low molecular weight heparin (LMWH), interferons including interferon alpha, interferon beta, interferon gamma, interleukin-2, luteinizing hormone releasing hormone (LHRH) and LHRH analogues including gosserelin, insulin, somatostatin, somatostatin analogs including octreotide, vasopressin and its analogs, follicle stimulating hormone (FSH), insulin-like growth factor, insulintropin, interleukin-1 receptor antagonist, interleukin-3, interleukin-4, interleukin-6, macrophage colony stimulating factor (M-CSF), nerve growth factor, parathyroid hormone (PTH), thymosin alpha 1, IIb/IIIa inhibitor, alpha-1 antitrypsin, VLA-4, respiratory syncytial virus antibody, cystic fibrosis transmembrane regulator (CFTR) gene, deoxyreibonuclease (Dnase), bactericidal/permeability increasing protein (BPI), anti-CMV antibody, interleukin-1 receptor, vaccines, 13-cis retinoic acid, pentamidine isethiouate, albuterol sulfate, metaproterenol sulfate, beclomethasone diprepionate, triamcinolone acetamide, budesonide acetonide, fluticasone, ipratropium bromide, flunisolide, cromolyn sodium, ergotamine tartrate and the analogues, agonists and antagonists of the above.

The amount of active agent to be encapsulated is dependent upon the type of substance, duration, time and desired effect. Drug loadings according to this invention range up to about 40 wt % (degree of loading=weight of active principal×100/weight of active principal+polymer weight).

Polymers suitable for practice of the present invention are known from the literature and include, for example, polyamides, polyanhydrides, polyesters, polyorthoesters, polyacetates, polylactones, and polyorthocarbonates. A preferred biodegradable polymer according to the invention comprises a polyester of α-, β- and γ-hydroxycarboxylic acids, or block copolymers of polyesters of α, β- and γ-hydroxycarboxylic acids and linear or star poly(ethylene glycols). Polylactide-co-glycolide polymers represent a particularly preferred class of polymers according to the invention.

Typically, a suitable polymer solution contains between about 1% (w/w) and about 50% (w/w) of a suitable biocompatible polymer, wherein the biocompatible polymer is typically dissolved in a suitable polymer solvent. Preferably, a polymer solution contains about 5% (w/w) to about 20% (w/w) polymer. The degradation rate for the microparticles of the invention is determined in part by the molecular weight of the polymer. Polymers of different molecular weights (or inherent viscosities) can be mixed to yield a desired degradation profile. According to a preferred embodiment, the degradation rate is controlled by the ratio of lactide to glycolide in the polymer.

Examples of biodegradable polymers for use with the process of the present invention are known in the art and include, but are not limited to, polyglycolides (PGA) and copolymers of glycolides such as glycolide/lactide copolymers (PGA/PLLA) or glycolide/trimethylene carbonate copolymers (PGA/TMC); L-polylactides (PLA) and stereo-copolymers of polylactides such as poly(L-lactide) (PLLA), poly(DL-lactide) copolymers and L-lactide/DL-lactide copolymers; copolymers of PLA such as lactide/tetramethylglycolide copolymers, lactide/δ-valerolactone copolymer and lactide/ε-caprolactone copolymer; poly(β-hydroxybutyrate) (PHBA), PHBA/β-hydroxyvalerate copolymers (PHBA/HVA), poly(β-hydroxypropionate) (PHPA), poly(p-dioxanone) (PDS), poly(δ-valerolactone), poly(ε-caprolactone), poly(polyamino acids), polysaccharides that have been rendered hydrophobic, or hyaluronic acid that has been rendered hydrophobic, or dextrans that have been rendered hydrophobic, or amylopectin or hyaluronic acid that have been rendered hydrophobic in a self-organizing manner.

AB block copolymers comprising PLA and PEG, ABA tri-block copolymers comprising PLA-PEG-PLA, S(3)-PEG-PLA block copolymers and S(4)-PEG-PLA block copolymers are suitable for use in the process in accordance with the invention as block copolymers of polyesters of hydroxycarboxylic acids and linear or star poly(ethylene glycol) (PEG):

Suitable commercially obtainable polymers for use according to the present invention include, but are not limited to Resomer® polylactide polymers and copolymers (Boehringer-Ingelheim) having the following product name designations: L104, L-206, L-207, L-208, L-209, L-210, L-214, R-104, R-202, R-203, R-206, R-207, R-208, G-110, 20G-205, LR-909, RG-502, RG-502H, RG-503, RG-503H, RG-504, RG 504H, RG-505, RG-505H, RG-506, RG-508, RG-752, RG-755, RG-756 and Resomer® RG-858.

Preferred solvents or solvent mixtures according to the invention include acetone, ethanol, alkyl acetates, such as methyl, ethyl, propyl, isopropyl, isobutyl or butyl acetate, alkyl formates, like methyl, ethyl, propyl, isopropyl or isobutyl formate, triacetin, triethyl citrate and/or C1–C4-alkyl lactates, e.g., methyl or ethyl lactates, methyl ethyl ketone, methyl isobutyl ketone, tetrahydrofuran, dimethyl sulfoxide, 1-methyl-2-pyrrolidone and 3-methyl-1-butanol, acetonitrile, THF, DMSO, PEG 100, PEG 400, N-methyl pyrrolidone, glycofurol, diethylcarbonate, and 2-methyl-1-propanol.

Preferred surfactants include cationic, anionic, and nonionic surfactants including, but not limited to Poloxamere® polyethylene-polypropylene glycol surfactant, Poloxamnine® polyalkoxylated symmetrical block polymers of ethylene diamine surfactant, polyethylene glycol alkyl ethers, polysorbates (Tween®, Span®), sucrose esters (Sisterna®, Netherlands), sucrose esters (Ryoto Sugar Ester, Tokyo), gelatins, polyvinylpyrrolidone, fatty alcohol polyglycosides, Charps, Charpso, decyl-P-D-glycopyranoside, decyl-P-D maltopyranoside, dodecyl-P-D-maltopyranoside, sodium oleate, polyethylene glycol, polyvinyl alcohol, polyctoxylated fatty acid ethers (Brij®), Triton X 10001 their mixtures. Amounts effective to provide a stable, aqueous formulation will be used, usually in the range of from about 0.1% (w/v) to about 30% (w/v).

The encapsulation efficiency of the process is at least 85%, preferably encapsulation efficiencies between 90 and 95% are achieved. Encapsulation efficiency is understood to mean the weight of the encapsulated active ingredient×100/weight of the employed active ingredient. Further, the present invention provides highly uniform morphologies such the resultant microparticles comprise at least 85%, preferably at least 90%, and most preferably greater than 95% of a single uniform morphology (i.e. at least 95% microcapsules).

The formulations of the instant invention can contain a preservative, multiple excipients, such as polyethylene glycol (PEG) in addition to polyols such as trehalose or mannitol. Examples of suitable preservatives for the formulation include phenol, benzyl alcohol, meta-cresol, methyl paraben, propyl paraben, benzalconium chloride, and benzethonium chloride. Preferred preservatives include about 0.2 to 0.4% (w/v) phenol and about 0.7 to 1% (w/v) benzyl alcohol, although the type of preservative and the concentration range are not critical.

In general, the drug phase, organic polymer solution, and/or surfactant phase of the subject invention can contain other components in amounts not detracting from the preparation of stable forms and in amounts suitable for effective, safe pharmaceutical administration. For example, other pharmaceutically acceptable excipients well known to those skilled in the art can form a part of the subject compositions. These include, for example, salts, various bulking agents, additional buffering agents, chelating agents, antioxidants, cosolvents and the like; specific examples of these include tris-(hydroxymethyl)aminomethane salts ("Tris buffer"), and disodium edetate. Cryo-protectors such as sugars, sugar alcohols or crystallization inhibitors, such as those disclosed in U.S. Pat. No. 5,676,968, such as low molecular weight polyvinylpyrrolidone and derivatives are optionally added for lyophilization.

According to a preferred use of the microparticles for pharmaceutical application, the microspheres are placed into pharmaceutically acceptable, sterile, isotonic formulations together with any required cofactors, and optionally are administered by standard means well known in the field. Microsphere formulations are typically stored as a dry powder. It is to be understood that the microparticles of the present invention could find use in other applications such as industrial chemicals, herbicides, fertilizers, and dyes.

The invention is further explained below in practical examples without restricting it to them. All of the above referenced patents are incorporated herein in their entirety by reference.

EXAMPLE 1

750 mg of the polymer Resomer® RG-756 is dissolved in 15 mL ethyl acetate and transferred to a double-walled steel vessel (inside height 11.0 cm, inside diameter 4 cm). 5 mL of an aqueous 200 mg HSA (human serum albumin)-containing, 5 mmol Tris(hydroxymethyl)aminomethane solution (pH 7.4) is then dispersed by means of a mechanical agitator (Dispermat FT, VMA-Getzmann GmbH, 2 cm dissolver disk) in the polymer solution for 3 minutes at 10,000 rpm at room temperature. 50 mL of a 4% Pluronic® F68 surfactant (which comprises block copolymers based on ethylene oxide and propylene oxide) solution in water is then added as continuous phase during agitation (10,000 rpm). After about 30 seconds of agitation, the microparticle suspension is transferred to a 500 mL two-necked flask and agitated with a magnetic stirrer. The solvent ethyl acetate is then eliminated at room temperature by applying a vacuum or by extraction with water. After 2 hours, the suspension is washed with 6 of water or an aqueous solution and concentrated by centrifuging or filtration to the desired volume. Purification and concentration can be conducted more gently by crossflow filtration with a Sartocon mini® (Sartorius AG, Gattingen) system.

The solvent- and almost surfactant-free suspension is mixed with a cryoprotector (for example, with a sugar, sugar alcohol or polyvinylpyrrolidone derivative), frozen as quickly as possible (for example, with liquid nitrogen) and freeze-dried. The lyophilizate, resuspended with water or an aqueous solution, contains microcapsules with a human serum albumin content of 18% (human serum albumin weight×100/human serum albumin weight+polymer weight=degree of loading) and these have a diameter from 0.2 to 8 μm. The encapsulation efficiency is 86%.

Figure 2A:

FIGS. 2a and 2b depict electron microscopic images of microcapsules produced in Example 1.

Figure 3B:
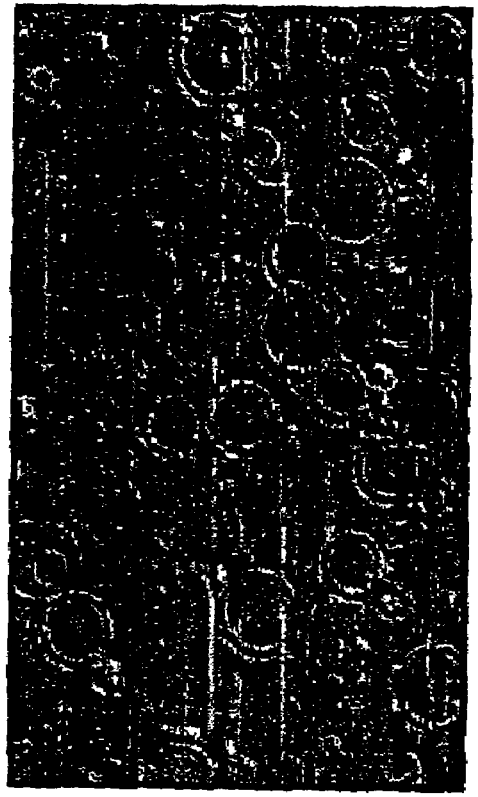
FIG. 3 depicts light microscopic images of microcapsules produced in Example 1.
Figure 3A:
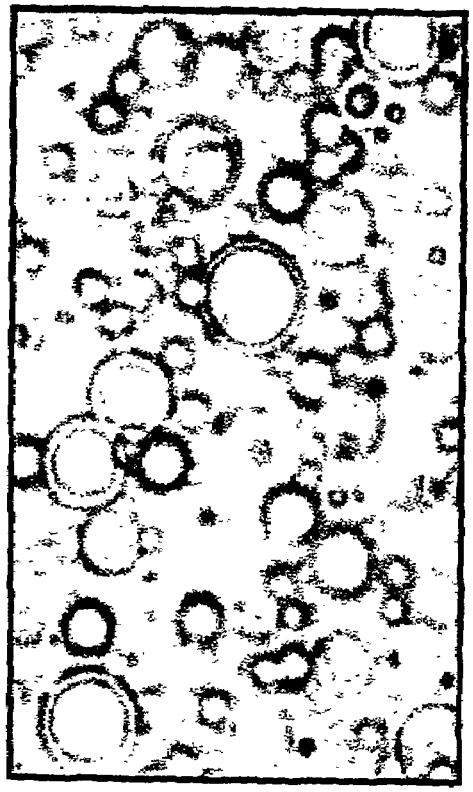

FIGS. 3a and 3b depict light microscopic images of microcapsules produced in Example 1.

EXAMPLE 2

750 mg of the polymer Resomer® RG-858 is dissolved in 15 mL ethyl acetate and transferred to a double-walled steel vessel (inside height 11.0 cm, inside diameter 4 cm). 5 m/L of an aqueous 50 mmol PBS buffer solution (pH 7.4) containing 100 mg HSA (human serum albumin) is then dispersed in the polymer solution for 3 minutes at 10,000 rpm by means of a mechanical agitator (Dispermat FT, VMA-Getzmann GmbH, 2 cm dissolver disk).

50 mL of a 4% Pluronic F127 solution in water is then added as continuous phase during agitation (10,000 rpm). After about 30 seconds of agitation, the microparticle suspension is transferred to a 500 mL two-necked flask and agitated with a magnetic stirrer. The microparticle suspension is further processed as in Example 1.

The lyophilizate, resuspended with water or an aqueous solution, contains microcapsules with a human serum albumin content of 10% (human serum albumin weight×100/human serum albumin weight+polymer weight=degree of loading) and these have a diameter from 0.2 to 15 μm. The encapsulation efficiency is 88%.

EXAMPLE 3

Polymer: RG-858, employed amount: 750 mg polymer is dissolved in 15 mL of the solvent listed in Table 1. Surfactant solution: volume: 50 mL, 2 g of the surfactant listed in Table 1 is dissolved in 50 mL of water.

HSA solution: 10 mg HSA is dissolved in 5 mL of a 10 mmol Tris(hydroxymethyl)aminomethane solution (pH 7.4).

Microcapsules loaded with HSA were produced from the components listed in this example according to the method described in Example 1. The lyophilizate, resuspended with water or with an aqueous solution, contains microcapsules with a diameter from 0.2 to 15 μm.

TABLE 1

| | T-707 | T-908 | Tween-80 | F-68 | F-127 | P-1570 | L-1695 |
|---|---|---|---|---|---|---|---|
| Methyl acetate | | | | | | | |
| Ethyl acetate | | | | | | | |
| Isopropyl acetate | | | | | | | |
| Ethyl formate | | | | | | | |
| Propyl formate | | | | | | | |

TABLE 1-continued

| | T-707 | T-908 | Tween-80 | F-68 | F-127 | P-1570 | L-1695 |
|---|---|---|---|---|---|---|---|
| Isopropyl formate | | | | | | | |
| Ethyl methyl ketone | | | | | | | |

The encapsulation efficiency in all the charges listed in Table 1 is at least 85%.

EXAMPLE 4

750 mg of the polymer Resomer® RG-752 is dissolved in 15 mL ethyl acetate and transferred to a double-walled steel vessel (inside height 11.0 cm, inside diameter 4 cm). 5 mL of an aqueous 5 mmol of an aqueous 50 mg ovalbumin-containing, 10 mmol PBS buffer solution (pH 7.4) is then dispersed in the polymer solution for 3 minutes at 9,000 rpm at room temperature by means of a mechanical agitator (Dispermat FT, VMA-Getzmann GmbH, 2 cm dissolver disk).

50 mL of a 4% Pluronic F127 solution in water is then added as continuous phase during agitation (9,000 rpm). After a dispersal time of 30 seconds, the microparticle suspension is transferred to a 500 mL two-necked flask and agitated with a magnetic stirrer. The solvent ethyl acetate is then eliminated at room temperature by application of vacuum, by introduction of nitrogen or air or by extraction with water. After 3 hours, the suspension is washed with 6 L water or an aqueous solution and concentrated by centrifuging or filtration to the desired volume. "Crossflow" filtration is carried out by means of a Sartocon mini® (Sartorius AG, Göttingen) system with a polyolefin membrane (cutoff 0.2 μm).

The solvent- and almost surfactant-free suspension is mixed with a cryoprotector (for example, with a sugar, sugar alcohol or polyvinylpyrrolidone derivative), frozen as quickly as possible (for example, with liquid nitrogen) and freeze-dried. The lyophilizate, resuspended with water or an aqueous solution, contains microcapsules with an active principle content of 5%. The microcapsules have a diameter from 0.2 to 20 μm. The encapsulation efficiency is 90%.

EXAMPLE 5

750 mg of the polymer Resomer® RG-503 is dissolved in 15 mL methyl acetate and transferred to a double-walled steel vessel (inside height 11.0 cm, inside diameter 4 cm). 5 mL of an aqueous 5 mmol of an aqueous 50 mg ovalbumin-containing, 10 mmol PBS buffer solution (pH 7.4) is then dispersed in the polymer solution for 3 minutes at 9,000 rpm at room temperature by means of a mechanical agitator (Dispermat FT, VMA-Getzmann GmbH, 2 cm dissolver disk).

45 mL of a 4% Poloxamin T-707 solution in water is then added as continuous phase during agitation (9,000 rpm). After a dispersal time of 30 seconds, the microparticle suspension is transferred to a 500 mL two-necked flask and further processed as in Example 4.

The lyophilizate, resuspended with water or an aqueous solution, contains microcapsules with an active principle content of 4.7%. The microcapsules have a diameter from 0.2 to 8 μm. The encapsulation efficiency is 87%.

EXAMPLE 6

Polymer: RG-858, employed amount: 750 mg polymer is dissolved in 15 mL of the solvent listed in Table 2. Surfactant solution: volume: 50 mL, 2 g of the surfactant listed in Table 2 is dissolved in 50 mL of water.

Ovalbumin solution: 10 mg ovalbumin is dissolved in 5 mL, 10 mmol Tris(hydroxymethyl)aminomethane solution (pH 7.4).

Microcapsules loaded with ovalbumin were produced from the components listed in this example according to the method described in Example 4. The lyophilizate, resuspended with water or with an aqueous solution, contains microcapsules with a diameter from 0.2 to 20 μm.

TABLE 2

| | T-707 | T-908 | Tween-80 | F-68 | F-127 | P-1570 | L-1695 |
|---|---|---|---|---|---|---|---|
| Methyl acetate | | | | | | | |
| Ethyl acetate | | | | | | | |
| Isopropyl acetate | | | | | | | |
| Ethyl formate | | | | | | | |
| Propyl formate | | | | | | | |
| Isopropyl formate | | | | | | | |
| Ethyl methyl ketone | | | | | | | |

The encapsulation efficiency in all the charges listed in Table 2 is at least 85%.

EXAMPLE 7

750 mg of the polymer Resomer® RG-752 is dissolved in 15 μL methyl acetate and transferred to a double-walled steel vessel (inside height 11.0 cm, inside diameter 4 cm). 5 mL of an aqueous 50 mmol citrate buffer solution (pH 6.6) containing 50 mg cytochrome C is then dispersed in the polymer solution for 3 minutes at 10,000 rpm at room temperature by means of a mechanical agitator (Dispermat FT, VMA-Getzmann GmbH, 2 cm dissolver disk).

50 mL of a 4% Poloxamin T-707 solution is then added as continuous phase during agitation at 10,000 rpm. After a dispersal time of 30 seconds, the microparticle suspension is transferred to a 500 mL two-necked flask and agitated with a magnetic stirrer. The solvent methyl acetate is then eliminated at 20° C. by application of vacuum, by introduction of nitrogen or air or by extraction with water. After 3 hours, the suspension is washed with 6 L water or an aqueous solution and concentrated to the desired volume by centrifuging or filtration. The use of "crossflow" filtration is advantageous, for example, with a Sartocon mini® (Sartorius AG, Göttingen) system with a polyolefin membrane (cutoff 0.2 µm).

The solvent- and almost surfactant-free suspension is mixed with a cryoprotector (for example, with a sugar, sugar alcohol or polyvinylpyrrolidone derivative), frozen as quickly as possible (for example, with liquid nitrogen) and freeze-dried. The lyophilizate, resuspended with water or an aqueous solution, contains microcapsules with an active principle content of 4.8%. The microcapsules have a diameter from 0.2 to 10 µm. The encapsulation efficiency is 87%.

EXAMPLE 8

750 mg of the polymer Resomer® RG-752 is dissolved in 15 mL ethyl methyl ketone and transferred to a double-walled steel vessel (inside height 11.0 cm, inside diameter 4 cm). 5 mL of a 50 mmol citrate buffer solution (pH 6.6) containing 50 mg cytochrome C is then dispersed in the polymer solution for 3 minutes at 8,000 rpm at room temperature by means of a mechanical agitator (Dispermat FT, VMA-Getzmann GmbH, 2 cm dissolver disk).

45 mL of 4% Tween-80 solution is then added at continuous phase during agitation (8,000 rpm). After a dispersal time of 30 seconds, the microparticle suspension is transferred to a 500 mL two-necked flask and further processed as in Example 7.

The lyophilizate, resuspended with water or an aqueous solution, contains microcapsules with an active principle content of 5%. The microcapsules have a diameter from 0.2 to 12 µm. The encapsulation efficiency is 90%.

EXAMPLE 9

Polymer: RG-858, employed amount: 750 mg polymer is dissolved in 15 mL of the solvent listed in Table 3.

Surfactant solution: volume: 50 mL, 2 g of the surfactant listed in Table 3 is dissolved in 50 mL of water.

Cytochrome-C solution: 10 mg cytochrome-C is dissolved in 5 mL of a 10 mmol Tris(hydroxymethyl)aminomethane solution (pH 7.4).

Microcapsules loaded with cytochrome-C were produced from the components listed in this example according to the method described in Example 7. The lyophilizate, resuspended with water or with an aqueous solution, contains microcapsules with a diameter from 0.2 to 12 µm.

The encapsulation efficiency in all the charges listed in Table 3 is at least 85%.

EXAMPLE 10

750 mg of the polymer Resomer® RG-503 is dissolved in 15 mL methyl acetate and transferred to a double-walled steel vessel (inside height 11.0 cm, inside diameter 4 cm). 5 mL of an aqueous solution (pH 7.5) containing 80 mg insulin is then dispersed in the polymer solution for 3 minutes at 10,000 rpm at room temperature by means of a mechanical agitator (Dispermat FT, VMA-Getzmann GmbH, 2 cm dissolver disk). 50 mL of a 4% Pluronic F-68 solution in water is then added as continuous phase during agitation at 10,000 rpm. After a dispersal time of 30 seconds, the microparticle suspension is transferred to a 500 mL two-necked flask and agitated with a magnetic stirrer. The solvent methyl acetate is then eliminated at 20° C. by application of vacuum, by introduction of nitrogen or air or by extraction with water. After 3 hours, the suspension is washed with 5 L water or an aqueous solution and concentrated to the desired volume by centrifuging or filtration. "Crossflow" filtration occurs, for example, with a Sartocon mini® (Sartorius AG, Göttingen) system with a polyolefin membrane (cutoff 0.2 µm).

The solvent- and almost emulsifier-free suspension is frozen as quickly as possible with liquid nitrogen and freeze-dried.

The lyophilizate, resuspended with water or an aqueous solution, contains microcapsules with an active principle content of 8%. The microcapsules have a diameter from 0.2 to 8 µm. The encapsulation efficiency is 90%.

EXAMPLE 11

750 mg of the polymer Resomer® RG-503 is dissolved in 15 mL methyl acetate and transferred to a double-walled steel vessel (inside height 11.0 cm, inside diameter 4 cm). 5 mL of an aqueous solution (pH 7.5) containing 60 mg insulin is then dispersed in the polymer solution for 3 minutes at 10,000 rpm at room temperature by means of a mechanical agitator (Dispermat FT, VMA-Getzmann GmbH, 2 cm dissolver disk). 50 mL of a 4% Pluronic F-127 solution in water is then added as continuous phase during agitation at 10,000 rpm. After a dispersal time of 30 seconds, the microparticle suspension is transferred to a 500 mL two-necked flask and processed further as in Example 10.

The lyophilizate, resuspended with water or an aqueous solution, contains microcapsules with an active principle content of 6%. The microcapsules have a diameter from 0.2 to 8 µm. The encapsulation efficiency is 85%.

TABLE 3

| | T-707 | T-908 | Tween-80 | F-68 | F-127 | P-1570 | L-1695 |
|---|---|---|---|---|---|---|---|
| Methyl acetate | | | | | | | |
| Ethyl acetate | | | | | | | |
| Isopropyl acetate | | | | | | | |
| Ethyl formate | | | | | | | |
| Propyl formate | | | | | | | |
| Isopropyl formate | | | | | | | |
| Ethyl methyl ketone | | | | | | | |

EXAMPLE 12

750 mg of the polymer Resomer® RG-503 is dissolved in 15 mL methyl acetate and transferred to a double-walled steel vessel (inside height 11.0 cm, inside diameter 4 cm). 5 mL or an aqueous solution (pH 3.2) containing 40 mg insulin is then dispersed in the polymer solution for 3 minutes at 10,000 rpm at room temperature by means of a mechanical agitator (Dispermat FT, VMA-Getzmann GmbH, 2 cm dissolver disk). 50 mL of a 4% Pluronic F-68 solution in water is then added as continuous phase during agitation at 10,000 rpm. After a dispersal time of 30 seconds, the microparticle suspension is transferred to a 500 mL two-necked flask and processed further as in Example 10.

The lyophilizate, resuspended with water or an aqueous solution, contains microcapsules with an active principle content of 4.4%. The microcapsules have a diameter from 0.2 to 8 μm. The encapsulation efficiency is 90%.

EXAMPLE 13

750 mg of the polymer Resomer® RG-503 is dissolved in 15 mL methyl acetate and transferred to a double-walled steel vessel (inside height 11.0 cm, inside diameter 4 cm). 5 mL of an aqueous solution (pH 3.0) containing 40 mg insulin is then dispersed in the polymer solution for 3 minutes at 10,000 rpm at room temperature by means of a mechanical agitator (Dispermat FT, VMA-Getzmann GmbH, 2 cm dissolver disk). 50 mL of a 4% Pluronic F-127 solution in water is then added as continuous phase during agitation at 10,000 rpm. After a dispersal time of 30 seconds, the microparticle suspension is transferred to a 500 mL two-necked flask and processed further as in Example 10.

The lyophilizate, resuspended with water or an aqueous solution, contains microcapsules with an active principle content of 4.4%. The microcapsules have a diameter from 0.2 to 8 μm. The encapsulation efficiency is 90%.

EXAMPLE 14

750 mg of the polymer Resomer® RG-503 is dissolved in 15 mL methyl acetate and transferred to a double-walled steel vessel (inside height 11.0 cm, inside diameter 4 cm). 5 mL of an aqueous solution (pH 7.5) containing 40 mg insulin is then dispersed in the polymer solution for 3 minutes at 10,000 rpm at room temperature by means of a mechanical agitator (Dispermat FT, VMA-Getzmann GmbH, 2 cm dissolver disk). 50 mL of a 50 mmol citrate buffer solution (pH 5.3, $IP_{insulin}$ pH 5.3) containing 2 g Pluronic F-68 is then added as continuous phase during agitation (10,000 rpm). After a dispersal time of 30 seconds, the microparticle suspension is transferred to a 500 mL two-necked flask and processed further as in Example 10.

The lyophilizate, resuspended with water or an aqueous solution, contains microcapsules with an active principle content of 4.8%. The microcapsules have a diameter from 0.2 to 8 μm. The encapsulation efficiency is 90%.

EXAMPLE 15

750 mg of the polymer Resomer® RG-503 is dissolved in 15 mL methyl acetate and transferred to a double-walled steel vessel (inside height 11.0 cm, inside diameter 4 cm). 5 mL or an aqueous solution (pH 7.5) containing 40 mg insulin is then dispersed in the polymer solution for 3 minutes at 10,000 rpm at room temperature by means of a mechanical agitator (Dispermat FT, VMA-Getzmann GmbH, 2 cm dissolver disk). 50 mL of a 50 mmol citrate buffer solution (pH 5.3, $IP_{insulin}$ pH 5.3) containing 2 g Pluronic F-127 is then added as continuous phase during agitation (10,000 rpm). After a dispersal time of 30 seconds, the microparticle suspension is transferred to a 500 mL two-necked flask and processed further as in Example 10.

The lyophilizate, resuspended with water or an aqueous solution, contains microcapsules with an active principle content of 4.8%. The microcapsules have a diameter from 0.2 to 8 μm. The encapsulation efficiency is 90%.

EXAMPLE 16

750 mg of the polymer Resomer® RG-503 is dissolved in 15 mL methyl acetate and transferred to a double-walled steel vessel (inside height 11.0 cm, inside diameter 4 cm). 5 mL or an aqueous solution (pH 7.5) containing 40 mg insulin is then dispersed in the polymer solution for 3 minutes at 10,000 rpm at room temperature by means of a mechanical agitator (Dispermat FT, VMA-Getzmann GmbH, 2 cm dissolver disk). 50 mL of a 2% Poloxamin T-908 solution in water is then added as continuous phase during agitation (10,000 rpm). After a dispersal time of 30 seconds, the microparticle suspension is transferred to a 500 mL two-necked flask and process further as in Example 10.

The lyophilizate, resuspended with water or an aqueous solution, contains microcapsules with an active principle content of 3.9%. The microcapsules have a diameter from 0.2 to 8 μm. The encapsulation efficiency is 90%.

EXAMPLE 17

750 mg of the polymer Resomer® RG-503 is dissolved in 15 mL methyl acetate and transferred to a double-walled steel vessel (inside height 11.0 cm, inside diameter 4 cm). 5 mL or an aqueous solution (pH 7.5) containing 20 mg insulin is then dispersed in the polymer solution for 3 minutes at 10,000 rpm at room temperature by means of a mechanical agitator (Dispermat FT, VMA-Getzmann GmbH, 2 cm dissolver disk). 50 mL of a 2% Poloxamin T-908 solution in water is then added as continuous phase during agitation (10,000 rpm). After a dispersal time of 30 seconds, the microparticle suspension is transferred to a 500 mL two-necked flask and process further as in Example 10.

The lyophilizate, resuspended with water or an aqueous solution, contains microcapsules with an active principle content of 2.2%. The microcapsules have a diameter from 0.2 to 8 μm. The encapsulation efficiency is 85%.

EXAMPLE 18

Polymer: RG-858, employed amount: 750 mg polymer is dissolved in 15 mL of the solvent listed in Table 4.

Surfactant solution: volume: 50 mL, 2 g of the surfactant listed in Table 4 is dissolved in 50 mL of water.

Insulin solution: 10 mg insulin is dissolved in 5 mL (pH 7.5).

Microcapsules loaded with insulin were produced from the components listed in this example according to the method described in Example 10. The lyophilizate, resuspended with water or with an aqueous solution, contains microcapsules with a diameter from 0.2 to 12 μm.

TABLE 4

| | T-707 | T-908 | Tween-80 | F-68 | F-127 | P-1570 | L-1695 |
|---|---|---|---|---|---|---|---|
| Methyl acetate | | | | | | | |
| Ethyl acetate | | | | | | | |
| Isopropyl acetate | | | | | | | |
| Ethyl formate | | | | | | | |
| Propyl formate | | | | | | | |
| Isopropyl formate | | | | | | | |
| Ethyl methyl ketone | | | | | | | |

The encapsulation efficiency in all the charges listed in Table 4 is at least 85%.

EXAMPLE 19

750 mg of the polymer Resomer® RG-858 is dissolved in 15 mL ethyl formate and transferred to a double-walled steel vessel (inside height 11.0 cm, inside diameter 4 cm). 5 mL of an aqueous 50 mmol Tris(hydroxymethyl)aminomethane solution (pH 7.5) containing 120 mg goserelin acetate (LHRH agonist) is then dispersed in the polymer solution for 4 minutes at 10,000 rpm at room temperature by means of a mechanical agitator (Dispermat FT, VMA-Getzmann GmbH, 2 cm dissolver disk). 50 mL of a 50 mmol citrate buffer solution (pH 6.0) containing 2 g Pluronic F-68 is then added as continuous phase during agitation at 10,000 rpm. After a dispersal time of 30 seconds, the microparticle suspension is transferred to a 500 mL two-necked flask and agitated with a magnetic stirrer. The solvent ethyl formate is then eliminated at 20° C. by applying a vacuum, by introduction of nitrogen or air or by extraction with water. After 5 hours, the suspension is washed with 5 L water or an aqueous solution and concentrated to the desired volume by centrifuging or filtration.

"Crossflow" filtration occurs with a Sartocon mini® (Sartorius AG, Göttingen) system with a polyolefin membrane (cutoff 0.2 Am). The solvent- and almost emulsifier-free suspension is frozen as quickly as possible with liquid nitrogen and freeze-dried.

The lyophilizate, resuspended with water or an aqueous solution, contains microcapsules with an active principle content of 12.5%. The microcapsules have a diameter from 0.2 to 12 μm. The encapsulation efficiency is 90%.

Figure 4:
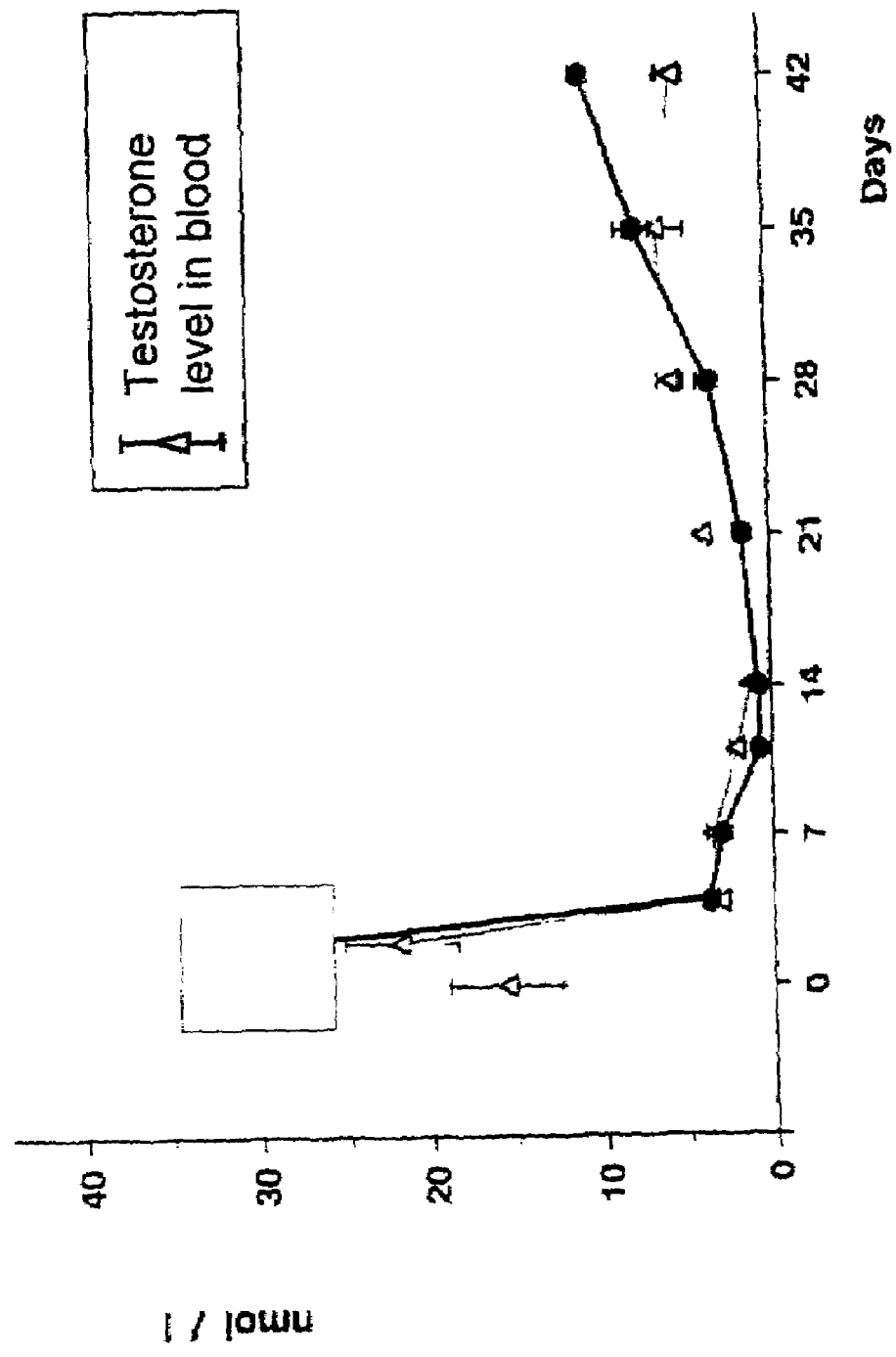
FIG. 4 depicts testosterone levels resulting from administration of gosserelin microparticles of Example 19.

FIG. 4 depicts testosterone levels resulting from administration of gosserelin microparticles of Example 19.

EXAMPLE 20

750 mg of the polymer Resomer® RG-503 is dissolved in 15 mL ethyl formate and transferred to a double-walled steel vessel (inside height 11.0 cm, inside diameter 4 cm). 5 mL of an aqueous 50 mmol Tris(hydroxymethyl)aminomethane solution (pH 7.5) containing 120 mg goserelin acetate (LHRH agonist) is then dispersed in the polymer solution for 4 minutes at 10,000 rpm at room temperature by means of a mechanical agitator (Dispermat FT, VMA-Getzmann GmbH, 2 cm dissolver disk).

50 mL of a 50 mmol citrate buffer solution (pH 6.0) containing 2 g Pluronic F-68 is then added as continuous phase during agitation at 10,000 rpm. After a dispersal time of 30 seconds, the microparticle suspension is transferred to a 500 mL two-necked flask and processed further as in Example 19.

The lyophilizate, resuspended with water or an aqueous solution, contains microcapsules with an active principle content of 12.5%. The microcapsules have a diameter from 0.2 to 8 μm. The encapsulation efficiency is 90%.

EXAMPLE 21

750 mg of the polymer Resomer® RG-756 is dissolved in 15 mL ethyl formate and transferred to a double-walled steel vessel (inside height 11.0 cm, inside diameter 4 cm). 5 mL of an aqueous 50 mmol Tris(hydroxymethyl)aminomethane solution (pH 7.5) containing 120 mg goserelin acetate (LHRH agonist) is then dispersed in the polymer solution for 4 minutes at 10,000 rpm at room temperature by means of a mechanical agitator (Dispermat FT, VMA-Getzmann GmbH, 2 cm dissolver disk).

50 mL of a 50 mmol citrate buffer solution (pH 6.0) containing 2 g Pluronic F-68 is then added as continuous phase during agitation at 10,000 rpm. After a dispersal time of 30 seconds, the microparticle suspension is transferred to a 500 ML two-necked flask and processed further as in Example 19.

The lyophilizate, resuspended with water or an aqueous solution, contains microcapsules with an active principle content of 12.5%. The microcapsules have a diameter from 0.2 to 12 μm. The encapsulation efficiency is 90%.

EXAMPLE 22

750 mg of the polymer Resomer® RG-756 is dissolved in 15 mL ethyl formate and transferred to a double-walled steel vessel (inside height 11.0 cm, inside diameter 4 cm). 5 mL of an aqueous 50 mmol Tris(hydroxymethyl)aminomethane solution (pH 7.5) containing 120 mg goserelin acetate (LHRH agonist) is then dispersed in the polymer solution for 4 minutes at 10,000 rpm at room temperature by means of a mechanical agitator (Dispermat FT, VMA-Getzmann GmbH, 2 cm dissolver disk). 50 mL of a 50 mmol citrate buffer solution (pH 6.0) containing 2 g Pluronic F-68, 3% sucrose and 7 g ethanol is then added as continuous phase during agitation at 10,000 rpm. After a dispersal time of 30 seconds, the microparticle suspension is transferred to a 500 mL two-necked flask and processed further as in Example 19.

The lyophilizate, resuspended with water or an aqueous solution, contains microcapsules with an active principle content of 12%. The microcapsules have a diameter from 0.2 to 10 μm. The encapsulation efficiency is 90%.

EXAMPLE 23

750 mg of the polymer Resomer® RG-756 is dissolved in 15 mL ethyl formate and transferred to a double-walled steel vessel (inside height 11.0 cm, inside diameter 4 cm). 5 mL of an aqueous 50 mmol Tris(hydroxymethyl)aminomethane solution (pH 7.5) containing 120 mg goserelin acetate (LHRH agonist) is then dispersed in the polymer solution for 4 minutes at 10,000 rpm at room temperature by means of a mechanical agitator (Dispermat FT, VMA-Getzmann GmbH, 2 cm dissolver disk).

50 mL of a 50 mmol citrate buffer solution (pH 6.0) containing 2 g Pluronic F-68 and 9 g ethanol is then added as continuous phase during agitation at 10,000 rpm. After a dispersal time of 30 seconds, the microparticle suspension is transferred to a 500 mL two-necked flask and processed further as in Example 19.

The lyophilizate, resuspended with water or an aqueous solution, contains microcapsules with an active principle content of 12%. The microcapsules have a diameter from 0.2 to 10 μm. The encapsulation efficiency is 90%.

Figure 5:
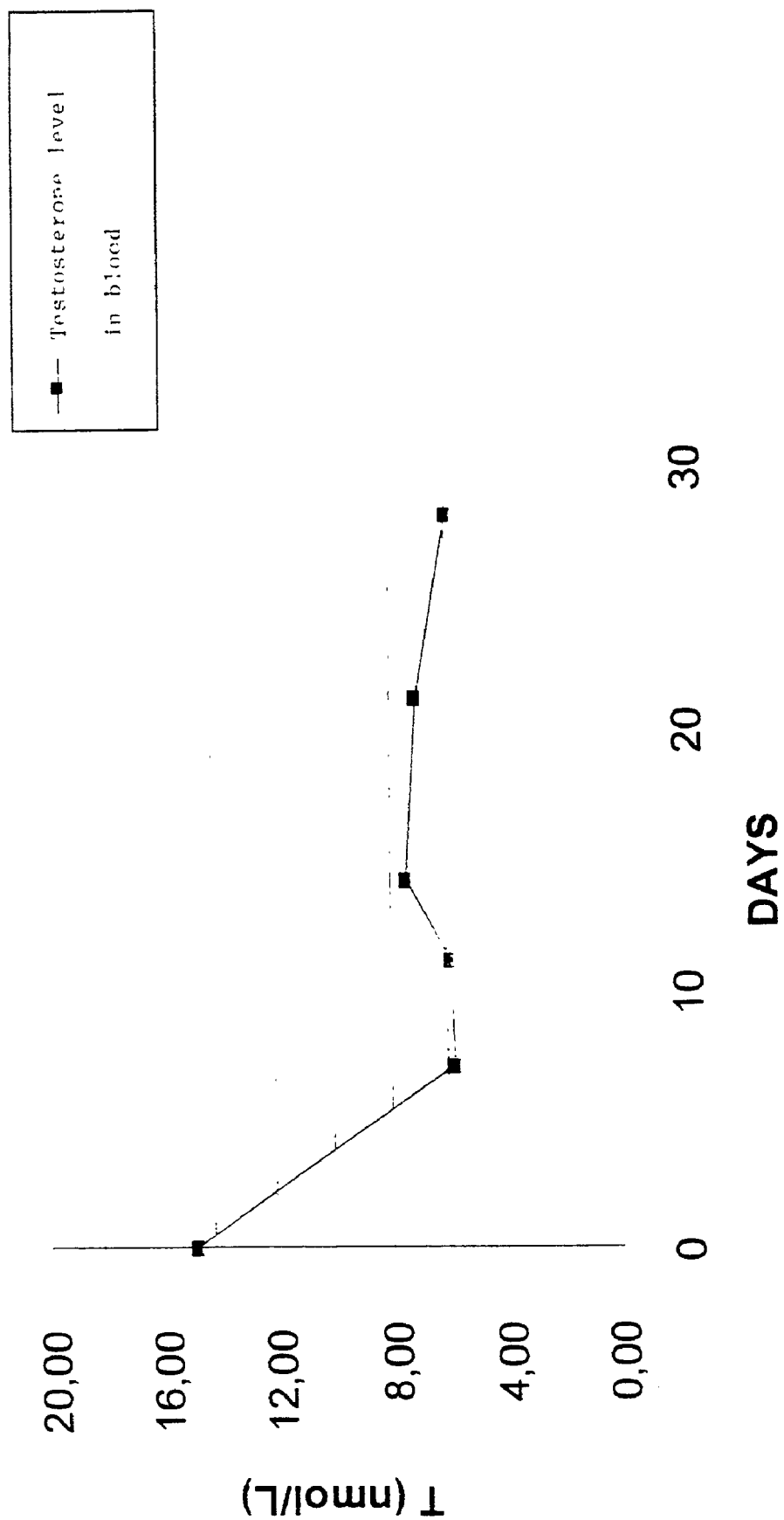
FIG. 5 depicts testosterone levels resulting from administration of gosserelin microparticles of Example 23.
Figure 6B:
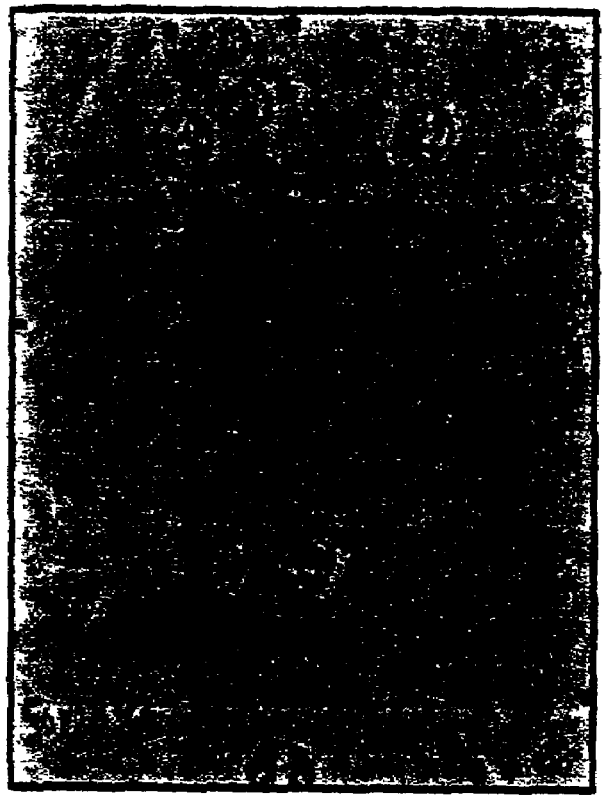
FIGS. 6a–d depict light microscopic images of microcapsules produced in Example 31/1–4.
Figure 6A:
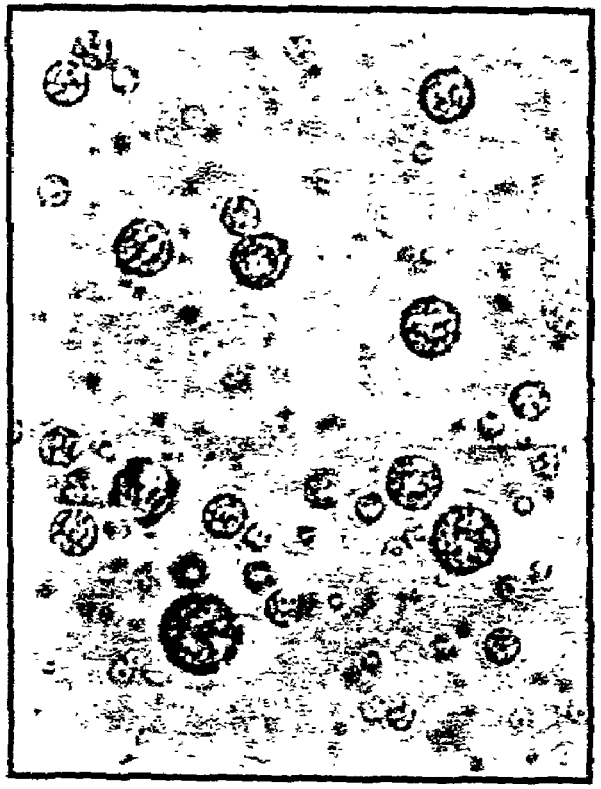
Figure 6C:
Figure 6D:

FIG. 5 depicts testosterone levels resulting from administration of gosserelin microparticles of Example 23.

EXAMPLE 24

750 mg of the polymer Resomer® RG-858 is dissolved in 15 mL ethyl formate and transferred to a double-walled steel vessel (inside height 11.0 cm, inside diameter 4 cm). 5 mL of an aqueous 50 mmol Tris(hydroxymethyl)aminomethane solution (pH 7.5) containing 120 mg goserelin acetate (LHRH agonist) is then dispersed in the polymer solution for 4 minutes at 10,000 rpm at room temperature by means of a mechanical agitator (Dispermat FT, VMA-Getzmann GmbH, 2 cm dissolver disk).

50 mL of a 50 mmol citrate buffer solution (pH 6.0) containing 4% Pluronic F-127 is then added as continuous phase during agitation at 10,000 rpm. After a dispersal time of 30 seconds, the microparticle suspension is transferred to a 500 mL two-necked flask and processed further as in Example 19.

The lyophilizate, resuspended with water or an aqueous solution, contains microcapsules with an active principle content of 12.5%. The microcapsules have a diameter from 0.2 to 15 μm. The encapsulation efficiency is 90%.

EXAMPLE 25

750 mg of the polymer Resomer® RG-858 is dissolved in 15 mL ethyl formate and transferred to a double-walled steel vessel (inside height 11.0 cm, inside diameter 4 cm). 5 mL of an aqueous 50 mmol succinate solution (pH 4.6) containing 120 mg goserelin acetate (LHRH agonist) is then dispersed in the polymer solution for 4 minutes at 10,000 rpm at room temperature by means of a mechanical agitator (Dispermat FT, VMA-Getzmann GmbH, 2 cm dissolver disk).

50 mL of a 50 mmol citrate buffer solution (pH 6.0) containing 4% Pluronic F-68 is then added as continuous phase during agitation at 10,000 rpm. After a dispersal time of 30 seconds, the microparticle suspension is transferred to a 500 mL two-necked flask and processed further as in Example 19.

The lyophilizate, resuspended with water or an aqueous solution, contains microcapsules with an active principle content of 12.5%. The microcapsules have a diameter from 0.2 to 15 μm. The encapsulation efficiency is 90%.

EXAMPLE 26

750 mg of the polymer Resomer® RG-858 is dissolved in 15 ML ethyl formate and transferred to a double-walled steel vessel (inside height 11.0 cm, inside diameter 4 cm). 5 mL of an aqueous 50 mmol Tris(hydroxymethl)amino methane solution (pH 7.4) containing 120 mg goserelin acetate (LHRH agonist) is then dispersed in the polymer solution for 4 minutes at 10,000 rpm at room temperature by means of a mechanical agitator (Dispermat FT, VMA-Getzmann GmbH, 2 cm dissolver disk). 50 mL of a 50 mmol citrate buffer solution (pH 6.0) containing 4% Pluronic F-68 is then added as continuous phase during agitation at 10,000 rpm. After a dispersal time of 30 seconds, the microparticle suspension is transferred to a 500 mL two-necked flask and processed further as in Example 19.

The lyophilizate, resuspended with water or an aqueous solution, contains microcapsules with an active principle content of 12.%. The microcapsules have a diameter from 0.2 to 15 μm. The encapsulation efficiency is 90%.

EXAMPLE 27

750 mg of the polymer Resomer® RG-503 is dissolved in 15 mL ethyl formate and transferred to a double-walled steel vessel (inside height 11.0 cm, inside diameter 4 cm). 5 mL of an aqueous 50 mmol citrate buffer solution (pH 6.0) containing 120 mg Buserelin acetate is then dispersed in the polymer solution for 4 minutes at 8,000 rpm at room temperature by means of a mechanical agitator (Dispermat FT, VMA-Getzmann GmbH, 2 cm dissolver disk).

50 mL of a 50 mmol citrate buffer solution (pH 6.0) containing 2 g Pluronic F-68 is then added as continuous phase during agitation at 8,000 rpm. After a dispersal time of 30 seconds, the microparticle suspension is transferred to a 500 mL two-necked flask and agitated with a magnetic stirrer. The solvent ethyl formate is then eliminated at 20° C. by application of vacuum, by introduction of nitrogen or air or by extraction with water. After 5 hours, the suspension is washed with 5 L water or an aqueous solution and concentrated to the desired volume by centrifuging or filtration.

"Crossflow" filtration occurs with a Sartocon mini® (Sartorius AG, Göttingen) system with a polyolefin membrane (cutoff 0.2 μm). The solvent- and almost emulsifier-free suspension is frozen as quickly as possible with liquid nitrogen and freeze-dried.

The lyophilizate, resuspended with water or an aqueous solution, contains microcapsules with an active principle content of 12.%. The microcapsules have a diameter from 0.2 to 10 μm. The encapsulation efficiency is 90%.

EXAMPLE 28

750 mg of the polymer Resomer® RG-585 is dissolved in 15 mL ethyl formate and transferred to a double-walled steel vessel (inside height 11.0 cm, inside diameter 4 cm). 5 mL of an aqueous 50 mmol Tris(hydroxymethyl)aminomethane solution (pH 7.0) containing 120 mg Triptorelin is then dispersed in the polymer solution for 4 minutes at 8,000 rpm at room temperature by means of a mechanical agitator (Dispermat FT, VMA-Getzmann GmbH, 2 cm dissolver disk).

50 mL of a 50 mmol citrate buffer solution (pH 6.0) containing 2 g Pluronic F-68 is then added as continuous phase during agitation at 8,000 rpm. After a dispersal time of 30 seconds, the microparticle suspension is transferred to a 500 mL two-necked flask and agitated with a magnetic stirrer. The solvent ethyl formate is then eliminated at 20° C. by application of vacuum, by introduction of nitrogen or air or by extraction with water. After 5 hours, the suspension is washed with 5 L water or an aqueous solution and concentrated to the desired volume by centrifuging or filtration.

"Crossflow" filtration occurs with a Sartocon mini® (Sartorius AG, Göttingen) system with a polyolefin membrane (cutoff 0.2 μm). The solvent- and almost emulsifier-free suspension is frozen as quickly as possible with liquid nitrogen and freeze-dried.

The lyophilizate, resuspended with water or an aqueous solution, contains microcapsules with an active principle content of 12.%. The microcapsules have a diameter from 0.2 to 15 μm. The encapsulation efficiency is 90%.

Example 29

750 mg of the polymer Resomer® RG-858 is dissolved in 15 mL ethyl formate and transferred to a double-walled steel vessel (inside height 11.0 cm, inside diameter 4 cm).

5 mL of an aqueous 50 mmol citrate buffer solution (pH 6.0) containing 120 mg Bromocriptine is then dispersed in the polymer solution for 4 minutes at 10,000 rpm at room temperature by means of a mechanical agitator (Dispermat FT, VMA-Getzmann GmbH, 2 cm dissolver disk).

50 mL of a 50 mmol citrate buffer solution (pH 6.0) containing 2 g Pluronic F-68 is then added as continuous phase during agitation at 10,000 rpm. After a dispersal time of 30 seconds, the microparticle suspension is transferred to a 500 mL two-necked flask and agitated with a magnetic stirrer. The solvent ethyl formate is then eliminated at 20° C. by application of vacuum, by introduction of nitrogen or air or by extraction with water. After 5 hours, the suspension is washed with 5 L water or an aqueous solution and concentrated to the desired volume by centrifuging or filtration.

"Crossflow" filtration occurs with a Sartocon mini® (Sartorius AG, Göttingen) system with a polyolefin membrane (cutoff 0.2 μm). The solvent- and almost emulsifier-free suspension is frozen as quickly as possible with liquid nitrogen and freeze-dried.

The lyophilizate, resuspended with water or an aqueous solution, contains microcapsules with an active principle content of 10.%. The microcapsules have a diameter from 0.2 to 15 μm. The encapsulation efficiency is 90%.

EXAMPLE 30

750 mg of the polymer Resomer® RG-858 is dissolved in 15 m/L ethyl formate and transferred to a double-walled steel vessel (inside height 11.0 cm, inside diameter 4 cm). 5 mL of an aqueous 50 mmol citrate buffer solution (pH 6.0) containing 100 mg Octreotide is then dispersed in the polymer solution for 4 minutes at 8,000 rpm at room temperature by means of a mechanical agitator (Dispermat FT, VMA-Getzmann GmbH, 2 cm dissolver disk).

50 mL of a 50 mmol citrate buffer solution (pH 6.0) containing 2 g Pluronic F-68 is then added as continuous phase during agitation at 8,000 rpm. After a dispersal time of 30 seconds, the microparticle suspension is transferred to a 500 mL two-necked flask and agitated with a magnetic stirrer. The solvent ethyl formate is then eliminated at 20° C. by application of vacuum, by introduction of nitrogen or air or by extraction with water. After 5 hours, the suspension is washed with 5 L water or an aqueous solution and concentrated to the desired volume by centrifuging or filtration.

"Crossflow" filtration occurs with a Sartocon mini® (Sartorius AG, Göttingen) system with a polyolefin membrane (cutoff 0.2 μm). The solvent- and almost emulsifier-free suspension is frozen as quickly as possible with liquid nitrogen and freeze-dried.

The lyophilizate, resuspended with water or an aqueous solution, contains microcapsules with an active principle content of 10.%. The microcapsules have a diameter from 0.2 to 15 μm. The encapsulation efficiency is 90%.

EXAMPLE 31

Microsponges:

Morphologically uniform microsponges are produced according to the standard method "induced phase transition method" as in Example 1, but without active principal. Volume of the polymer solution: 750 mg of the corresponding polymer in Table 5 is dissolved in 15 mL of the organic solvent listed in Table 5. Inner phase: 5 mL PBS, pH 7.4 (50 mmol)

Continuous surfactant phase: 50 mL aqueous solution contains 2 g of the surfactant listed in Table 5.

Microsponges were produced from the components listed in this example according to the method described in Example 1. The lyophilizate, resuspended with water or an aqueous solution, contains microsponges with a diameter from 0.2 to 20 μm.

TABLE 5

| Example No. | 31/1 | 31/2 | 31/3 | 31/4 |
|---|---|---|---|---|
| Polymer | R-202 | RG-503 | RG-755 | RG-858 |
| Organic solvent | Isopropyl acetate | Methyl acetate | Methyl acetate | Isopropyl acetate |
| Inner aqueous phase | PBS | PBS | PBS | PBS |
| Continuous surfactant phase | T-908 | Tween-20 | Tween-80 | F-68 |

FIGS. 6a–d depict light microscopic images of microcapsules produced in Example 31/1–4.

Figure 7A:
FIGS. 7a–b depict electron microscope images of the microsponges produced in Examples 31/2 and 31/3.
Figure 7B:
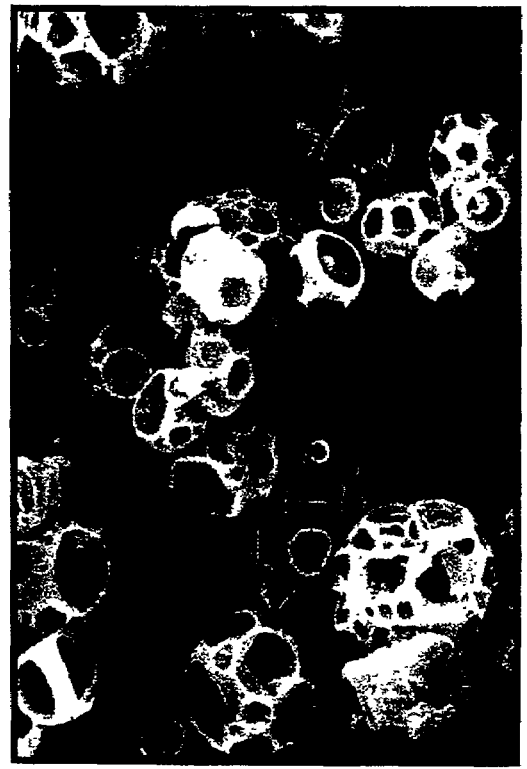

FIGS. 7a–b depict electron microscope images of the microsponges produced in Examples 31/2 and 31/3.

EXAMPLE 32

Monolithic microspheres.

Morphologically uniform monolithic microspheres are produced according to the standard method "induced phase transition method" as in Example 1, but without active principal.

Volume of the polymer solution: 750 mg of the corresponding polymer in Table 6 is dissolved in 15 mL of the organic solvent listed in Table 6.

Inner phase: 5 mL PBS, pH 7.4 (50 mmol) or citrate buffer pH 6.5 (50 mmol) Continuous surfactant phase: 50 mL aqueous solution contains 2 g of the surfactant listed in Table 6.

Monolithic microspheres were produced from the components listed in this example according to the method described in Example 1. The lyophilizate, resuspended with water or an aqueous solution, contains monolithic microspheres with a diameter from 0.2 to 20 μm.

TABLE 6

| Example No. | 32/1 | 32/2 | 32/3 | 32/4 |
|---|---|---|---|---|
| Polymer | R-202 | RG-503 | RG-752 | RG-858 |
| Organic solvent | Isopropyl acetate | Ethyl formate | Isopropyl acetate | Isopropyl acetate |
| Inner aqueous phase | PBS | PBS | PBS | Citrate |
| Continuous surfactant phase | F-68 | Tween-20 | Tween-80 | Tween-80 |

Figure 8B:
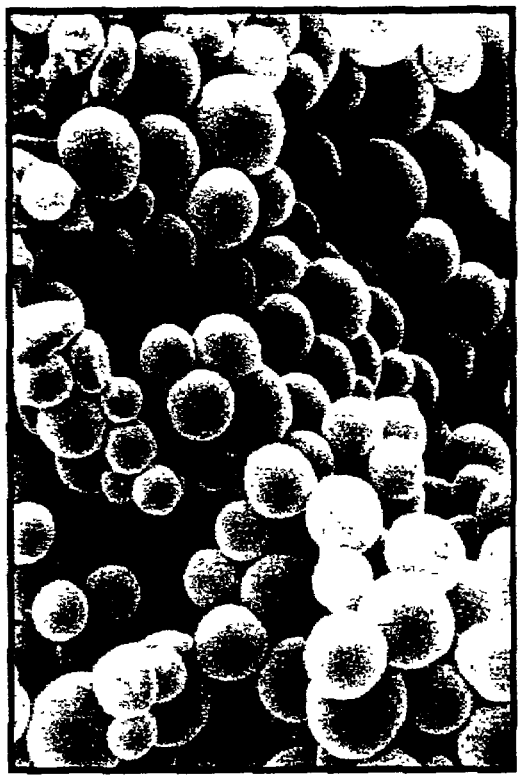
FIGS. 8a–b depict electron microscope images of microspheres produced in Examples 32/2 and 32/3.
Figure 8A:
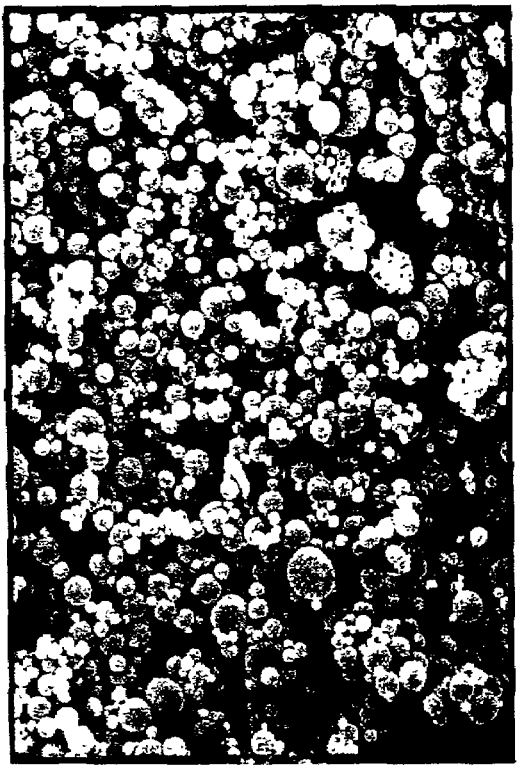

FIGS. 8a–b depict electron microscope images of microspheres produced in Examples 32/2 and 3213.

EXAMPLE 33

Microcapsules

Morphologically uniform microcapsules are produced according to the standard method "induced phase transition method" as in Example 1, but without active principal. Volume of the polymer solution: 750 mg of the corresponding polymer in Table 7 is dissolved in 15 mL of the organic solvent listed in Table 7.

Inner phase: 5 mL PBS, pH 7.4 (50 mmol) or citrate buffer pH 6.5 (50 mmol) or Tris buffer pH 9 (50 mmol).

Continuous surfactant phase: 50 mL aqueous solution contains 2 g of the surfactant listed in Table 7.

Microcapsules were produced from the components listed in this example according to the method described in Example 1. The lyophilizate, resuspended with water or an aqueous solution, contains monolithic microspheres with a diameter from 0.2 to 20 µm.

TABLE 7

| Polymer | R-203 | RG-502H | RG-755 | RG-858 |
|---|---|---|---|---|
| Organic solvent | Ethyl formate | Ethyl methyl ketone | Methyl acetate | Ethyl acetate |
| Inner aqueous phase | PBS | Citrate | Tris | Citrate |
| Continuous surfactant phase | F-127 | F-68 | F-127 | F-68 |

EXAMPLE 34

750 mg of the polymer Resomer® RG-756 are dissolved in 15 ml of ethyl acetate and transferred to a double wall steel vessel (internal height 11 cm; internal diameter 4 cm). 5 ml of an aqueous 5 millimolar tris(hydroxymethyl)aminomethane solution (pH 7.4), which contains 200 mg of HSA (human serum albumin), are then dispersed in the polymer solution with the help of a mechanical stirrer (Dispermat-FT, VMA-Getzmann GmbH; 2 cm dissolver disk) over a period of 3 minutes at 10,000 RPM at room temperature. 50 ml of a solution comprising 4% Pluronic F-68 in a mixture of water and glycerin (1:1) are then added, with stirring (10,000 RPM), as the continuous phase. After stirring for approximately 30 seconds, the suspension of micro-particles is transferred to a 500 ml double neck flask and stirred by means of a magnetic stirrer. The ethyl acetate solvent is then removed at room temperature by applying a vacuum or by means of extraction with water. After 2 hours, the suspension is washed with 6 liters of water or an aqueous solution and evaporatively concentrated to the desired volume with the help of centrifugation or filtration.

The purification and evaporative concentration can be carried out more gently with the help of "cross flow" filtration by means of a Sartocon mini® system (Sartorius AG, Göttingen).

The suspension, which is solvent-free and approximately surfactant-free, is mixed with a cryo-protector (for example: with a sugar, sugar alcohol or polyvinylpyrrolidone derivative) and then frozen as rapidly as possible, e.g. with liquid nitrogen, and freeze dried. The lyophilisate, which is re-suspended with water or an aqueous solution, contains micro-particles with a human serum albumin content of 20% and a diameter of 0.2 to 5 µm.

EXAMPLE 35

750 mg of the polymer Resomer® RG-503 are dissolved in 15 ml of ethyl formate and transferred to a double wall steel vessel (internal height 11 cm; internal diameter 4 cm). 5 ml of an aqueous 50 millimolar PBS buffer solution (pH 7.4), which contains 100 mg of HSA (human serum albumin), are then dispersed in the polymer solution with the help of a mechanical stirrer (Dispermat-FT, VMA-Getzmann GmbH; 2 cm dissolver disk) over a period of 3 minutes at 10,000 RPM at room temperature.

50 ml of a solution comprising 4% Pluronic F-68 in a mixture of water and glycerin (40:60) are then added, with stirring (10,000 RPM), as the continuous phase. After stirring for approximately 30 seconds, the suspension of micro-particles is transferred to a 500 ml double neck flask and stirred by means of a magnetic stirrer.

The suspension of micro-particles is processed further as in Example 34.

The lyophilisate, which is re-suspended with water or an aqueous solution, contains micro-particles with a human serum albumin content of 10% and a diameter of 0.2 to 5 µm.

EXAMPLE 36

Polymer: RG-858; quantity used: 750 mg of polymer are dissolved in 15 ml, in each case, of the solvents that are listed in Table 8.

Surfactant solution: volume: 50 ml; 2 g of each surfactant that is listed in Table 8 are dissolved in 50 ml of a mixture of water and glycerin (20:80).

HSA solution: 100 mg of HSA are dissolved in 5 ml of a 10 millimolar tris(hydroxymethyl)aminomethane solution (pH 7.4).

Micro-capsules, which are charged with HSA and which comprise the components that are listed in this example, were prepared in accordance with the method that is described in Example 34. The lyophilisate, which is re-suspended with water or an aqueous solution, contains micro-particles with a diameter of 0.2 to 5 µm.

TABLE 8

| | T-707 | T-908 | Tween-80 | F-68 | F-127 | P-1570 | L-1695 |
|---|---|---|---|---|---|---|---|
| Methyl acetate | | | | | | | |
| Ethyl acetate | | | | | | | |
| Isopropyl acetate | | | | | | | |
| Ethyl formate | | | | | | | |
| Propyl formate | | | | | | | |

TABLE 8-continued

| | T-707 | T-908 | Tween-80 | F-68 | F-127 | P-1570 | L-1695 |
|---|---|---|---|---|---|---|---|
| Isopropyl formate | | | | | | | |
| Ethyl methyl ketone | | | | | | | |

The concentration of HSA amounts to 10% (w/w) in all the formulations that are listed in Table 8.

EXAMPLE 37

750 mg of the polymer Resomer® RG-752 are dissolved in 15 ml of ethyl acetate and transferred to a double wall steel vessel (internal height 11 cm; internal diameter 4 cm). 5 ml of an aqueous 10 millimolar PBS buffer solution (pH 7.4), which contains 50 mg of egg albumin, are then dispersed in the polymer solution with the help of a mechanical stirrer (Dispermat-FT, VMA-Getzmann GmbH; 2 cm dissolver disk) over a period of 3 minutes at 9,000 RPM at room temperature.

50 ml of a solution comprising 4% Pluronic F-127 in a mixture of water and glycerin (25:75) are then added, with stirring (9,000 RPM), as the continuous phase. After a dispersing time of 30 seconds, the suspension of microparticles is transferred to a 500 ml double neck flask and stirred by means of a magnetic stirrer. The ethyl acetate solvent is then removed at room temperature by applying a vacuum, or by admitting nitrogen or air, or by means of extraction with water. After 3 hours, the suspension is washed with 6 liters of water or an aqueous solution and evaporatively concentrated to the desired volume with the help of centrifugation or filtration. "Cross flow" filtration is carried out by means of a Sartocon mini® system (Sartorius AG, Göttingen) with a polyolefin membrane (cut off 0.2 µm).

The suspension, which is solvent-free and approximately emulsifier-free, is mixed with a cryo-protector (for example: with a sugar, sugar alcohol or polyvinylpyrrolidone derivative) and then frozen as rapidly as possible, e.g. with liquid nitrogen, and freeze dried.

The lyophilisate, which is re-suspended with water or an aqueous solution, contains micro-particles with a 5.5% concentration of the active substance. And a diameter of 0.2 to 5 µm.

EXAMPLE 38

750 mg of the polymer Resomer® RG-503 are dissolved in 15 ml of methyl acetate and transferred to a double wall steel vessel (internal height 11 cm; internal diameter 4 cm). 5 ml of an aqueous 10 millimolar PBS buffer solution (pH 7.4), which contains 50 mg of egg albumin, are then dispersed in the polymer solution with the help of a mechanical stirrer (Dispermat-FT, VMA-Getzmann GmbH; 2 cm dissolver disk) over a period of 3 minutes at 9,000 RPM at room temperature.

50 ml of a solution comprising 4% Poloxamin T-707 in a mixture of water and glycerin (20:80) are then added, with stirring (9,000 RPM), as the continuous phase. After a dispersing time of 30 seconds, the suspension of microparticles is transferred to a 500 ml double neck flask and processed further as in Example 37.

The lyophilisate, which is re-suspended with water or an aqueous solution, contains micro-particles with a 5.5% concentration of the active substance and a diameter of 0.2 to 5 µm.

EXAMPLE 39

750 mg of the polymer Resomer® RG-503 are dissolved in 15 ml of methyl acetate and transferred to a double wall steel vessel (internal height 11 cm; internal diameter 4 cm). 5 ml of an aqueous solution (pH 7.5), which contains 80 mg of insulin, are then dispersed in the polymer solution with the help of a mechanical stirrer (Dispermat-FT, VMA-Getzmann GmbH; 2 cm dissolver disk) over a period of 3 minutes at 10,000 RPM at room temperature.

50 ml of a solution comprising 4% Pluronic F-68 in a mixture of water and glycerin (20:80) are then added, with stirring (10,000 RPM), as the continuous phase. After a dispersing time of 30 seconds, the suspension of microparticles is transferred to a 500 ml double neck flask and stirred by means of a magnetic stirrer. The methyl acetate solvent is then removed at 20° C. by applying a vacuum, or by admitting nitrogen or air, or by means of extraction with water. After 3 hours, the suspension is washed with 5 liters of water or an aqueous solution and evaporatively concentrated to the desired volume with the help of centrifugation or filtration. "Cross flow" filtration takes place e.g. by means of a Sartocon mini® system (Sartorius AG, Göttingen) with a polyolefin membrane (cut off 0.2 am). The suspension, which is solvent-free and approximately emulsifier-free, is frozen as rapidly as possible with liquid nitrogen, and freeze dried.

The lyophilisate, which is re-suspended with water or an aqueous solution, contains micro-capsules with a 8.5% concentration of the active substance. The micro-capsules possess a diameter of 0.2 to 5 µm.

EXAMPLE 40

750 mg of the polymer Resomer® RG-503 are dissolved in 15 ml of methyl acetate and transferred to a double wall steel vessel (internal height 11 cm; internal diameter 4 cm). 5 ml of an aqueous solution (pH 7.5), which contains 60 mg of insulin, are then dispersed in the polymer solution with the help of a mechanical stirrer (Dispermat-FT, VMA-Getzmann GmbH; 2 cm dissolver disk) over a period of 3 minutes at 10,000 RPM at room temperature.

50 ml of a solution comprising 4% Pluronic F-127 in a mixture of water and glycerin (20:80) are then added, with stirring (10,000 RPM), as the continuous phase. After a dispersing time of 30 seconds, the suspension of microparticles is transferred to a 500 ml double neck flask and processed further as in Example 39.

The lyophilisate, which is re-suspended with water or an aqueous solution, contains micro-particles with a 6.5% concentration of the active substance and a diameter of 0.2 to 5 µm.

EXAMPLE 41

750 mg of the polymer Resomer® RG-503 are dissolved in 15 ml of methyl acetate and transferred to a double wall steel vessel (internal height 11 cm; internal diameter 4 cm). 5 ml of an aqueous solution (pH 3.2), which contains 40 mg of insulin, are then dispersed in the polymer solution with the help of a mechanical stirrer (Dispermat-FT, VMA-Getzmann GmbH; 2 cm dissolver disk) over a period of 3 minutes at 10,000 RPM at room temperature.

50 ml of a solution comprising 4% Pluronic F-68 in a mixture of water and glycerin (20:80) are then added, with stirring (10,000 RPM), as the continuous phase. After a dispersing time of 30 seconds, the suspension of micro-particles is transferred to a 500 ml double neck flask and processed further as in Example 39.

The lyophilisate, which is re-suspended with water or an aqueous solution, contains micro-particles with a 4.8% concentration of the active substance and a diameter of 0.2 to 5 µm.

EXAMPLE 42

750 mg of the polymer Resomer® RG-503 are dissolved in 15 ml of methyl acetate and transferred to a double wall steel vessel (internal height 11.0 cm; internal diameter 4 cm). 5 ml of an aqueous solution (pH 3.0), which contains 40 mg of insulin, are then dispersed in the polymer solution with the help of a mechanical stirrer (Dispermat-FT, VMA-Getzmann GmbH; 2 cm dissolver disk) over a period of 3 minutes at 10,000 RPM at room temperature.

50 ml of a solution comprising 4% Pluronic F-127 in a mixture of water and glycerin (20:80) are then added, with stirring (10,000 RPM), as the continuous phase. After a dispersing time of 30 seconds, the suspension of micro-particles is transferred to a 500 ml double neck flask and processed further as in Example 39.

The lyophilisate, which is re-suspended with water or an aqueous solution, contains micro-particles with a 4.8% concentration of the active substance and a diameter of 0.2 to 4 µm.

EXAMPLE 43

750 mg of the polymer Resomer® RG-503 are dissolved in 15 ml of methyl acetate and transferred to a double wall steel vessel (internal height 11.0 cm; internal diameter 4 cm). 5 ml of an aqueous solution (pH 7.5), which contains 40 mg of insulin, are then dispersed in the polymer solution with the help of a mechanical stirrer (Dispermat-FT, VMA-Getzmann GmbH; 2 cm dissolver disk) over a period of 3 minutes at 10,000 RPM at room temperature.

50 ml of a solution comprising 4% Pluronic F-68 in a mixture comprising 50 millimolar citrate buffer of pH=6.6 and glycerin (80:20) are then added, with stirring (10,000 RPM), as the continuous phase. After a dispersing time of 30 seconds, the suspension of micro-particles is transferred to a 500 ml double neck flask and processed further as in Example 39.

The lyophilisate, which is re-suspended with water or an aqueous solution, contains micro-particles with a 4.8% concentration of the active substance and a diameter of 0.2 to 4 µm.

EXAMPLE 44

750 mg of the polymer Resomer® RG-503 are dissolved in 15 ml of methyl acetate and transferred to a double wall steel vessel (internal height 11.0 cm; internal diameter 4 cm). 5 ml of an aqueous solution (pH 7.5), which contains 40 mg of insulin, are then dispersed in the polymer solution with the help of a mechanical stirrer (Dispermat-FT, VMA-Getzmann GmbH; 2 cm dissolver disk) over a period of 3 minutes at 10,000 RPM at room temperature.

50 ml of a solution comprising 4% Pluronic F-127 in a mixture comprising 50 millimolar citrate buffer of pH=6.6 and glycerin (60:40) are then added, with stirring (10,000 RPM), as the continuous phase. After a dispersing time of 30 seconds, the suspension of micro-particles is transferred to a 500 ml double neck flask and processed further as in Example 39.

The lyophilisate, which is re-suspended with water or an aqueous solution, contains micro-particles with a 4.8% concentration of the active substance and a diameter of 0.2 to 4 µm.

EXAMPLE 45

2250 mg of the polymer Resomer® RG 504 is dissolved in 15 ml of a solvent mixture, consisting of 70 vol.-% ethylformate and 30 vol.-% acetone, and transferred to a glass vessel (inside height 10.5 cm, inside diameter 4.5 cm). 4 ml of an aqueous 150 mg eST (equine Somatotropine)-containing, 100 mmol/l glycine-buffered solution (pH 12), containing 0.1% (w/v) polysorbate 20, is then dispersed by means of a mechanical agitator (Dispermat FT, VMA Getzmann GmbH, 3.2 cm dissolver disc) in the polymer solution for 3 minutes at 6,000 rpm at room temperature.

100 ml of a 4% pluronic F-68 solution in a citrate-buffer, 50 mmol/ with a pH of 5.4, is then added as continuous phase during agitation (6,000 rpm). After 60 seconds of agitation, the microparticle suspension is transferred to a 1000 ml two necked-flask and agitated with a magnetic stirrer. The solvents, ethylformate and acetone, are eliminated at room temperature by applying vacuum or by extraction with water. After 2 hours, the suspension is washed with app. 600 ml of water or an aqueous solution and concentrated by centrifuging or filtration to the desired volume.

The solvent- and almost surfactant-free suspension is diluted with water or mixed with a solution of a cryoprotector (for example, with a sugar), frozen as quickly as possible (for example, with liquid nitrogen or by placing in a −80° C. freezer) and freeze-dried. The lyophilizate, resuspended with water or an aqueous solution, contains micro-particles with an equine Somatotropin content of 6.0% (equine Somatotropin weight×100/equine Somatotropin weight+polymer weight=degree of loading) and these have a diameter of 5 to 10 µm. The encapsulation efficiency is at least 95%.

EXAMPLE 46

2250 mg of the polymer Resomer® RG 504 is dissolved in 15 ml of a solvent mixture, consisting of 70 vol.-% ethyl formate and 30 vol.-% acetone, and transferred to a glass vessel (inside height 10.5 cm, inside diameter 4.5 cm). 4 ml of an aqueous 300 mg eST (equine Somatotropine)-containing, 100 mmol/l glycine-buffered solution (pH 12), containing 0.1% (w/v) polysorbate 20, is then dispersed by means of a mechanical agitator (Dispermat FT, VMA Getzmann GmbH, 3.2 cm dissolver disc) in the polymer solution for 3 minutes at 6,000 rpm at room temperature.

100 ml of a 4% pluronic F-68 solution in a citrate-buffer, 50 mmol/l with a pH of 5.4, is then added as continuous phase during agitation (6,000 rpm). After 60 seconds of agitation, the microparticle suspension is transferred to a 1000 ml two necked-flask and agitated with a magnetic stirrer. The solvents, ethyl formate and acetone, will then eliminated at room temperature by applying a vacuum or by extraction with water. After 2 hours, the suspension is washed with ca. 600 ml of water or an aqueous solution and concentrated by centrifuging or filtration to the desired volume.

The solvent- and almost surfactant-free suspension is thinned down with water or mixed with a solution of a cryoprotector (for example, with a sugar), frozen as quickly as possible (for example, with liquid nitrogen or by placing in a −80° C. freezer) and freeze-dried. The lyophilizate, resuspended with water or an aqueous solution, contains microparticles with an equine Somatotropin content of 11.0% (equine Somatotropin weight×100/equine Somatotropin weight+polymer weight=degree of loading) and these have a diameter of 5 to 13 µm. The encapsulation efficiency is at least 90%.

EXAMPLE 47

2250 mg of the polymer Resomer® RG 504 is dissolved in 15 ml of a solvent mixture, consisting of 70 vol.-% ethyl formate and 30 vol.-% acetone, and transferred to a glass vessel (inside height 10.5 cm, inside diameter 4.5 cm). 4 ml of an aqueous 450 mg eST (equine Somatotropine)-containing, 100 mmol/l glycine-buffered solution (pH 12), containing 0.1% (w/v) polysorbate 20, is then dispersed by means of a mechanical agitator (Dispermat FT, VMA Getzmann GmbH, 3.2 cm dissolver disc) in the polymer solution for 3 minutes at 6,000 rpm at room temperature.

100 ml of a 4% pluronic F-68 solution in a citrate-buffer, 50 mmol/l with a pH of 5.4, is then added as continuous phase during agitation (6,000 rpm). After 60 seconds of agitation, the microparticle suspension is transferred to a 1000 ml two necked-flask and agitated with a magnetic stirrer. The solvents, ethyl formate and acetone, are eliminated at room temperature by applying vacuum or by extraction with water. After 2 hours, the suspension is washed with app. 600 ml of water or an aqueous solution and concentrated by centrifuging or filtration to the desired volume.

The solvent- and almost surfactant-free suspension is diluted with water or mixed with a solution of a cryoprotector (for example, with a sugar), frozen as quickly as possible (for example, with liquid nitrogen or by placing in a −80° C. freezer) and freeze-dried. The lyophilizate, resuspended with water or an aqueous solution, contains microparticles with an equine Somatotropin content of 16.0% (equine Somatotropin weight×100/equine Somatotropin weight+polymer weight=degree of loading) and these have a diameter of 5 to 25 µm. The encapsulation efficiency is at least 90%.

EXAMPLE 48

The microparticles of Examples 45–47 were evaluated in in vitro release tests. 9.8–10.2 mg of the freeze-dried microparticles were weighed into 25 ml-lyophilization vials. Two vials were tested per time point, and the appropriate number of vials to perform up to a four weeks in-vitro release study was prepared. 5 ml of 50 mmol/l phosphate buffered saline (PBS), of pH 7.4, containing 0.1% Sodium azide and 0.1% polysorbate 20, was added and the vials were placed on an orbital shaker at 130 rpm and 37 C. On predefined time intervals 2 vials per time point were removed. The microparticles were separated from the release medium by centrifugation, washed two times with 4 ml of bi-distilled water and were again centrifuged. The wet pellet was freeze-dried over night. The dried remainder was accurately weighed into lyophilization vials and dissolved in dimethyl sulfoxide. This solution was filtered through 0.22-µm filters prior to analysis and then assayed for eST content using a reversed phase liquid chromatography (HPLC) method.

Figure 9:
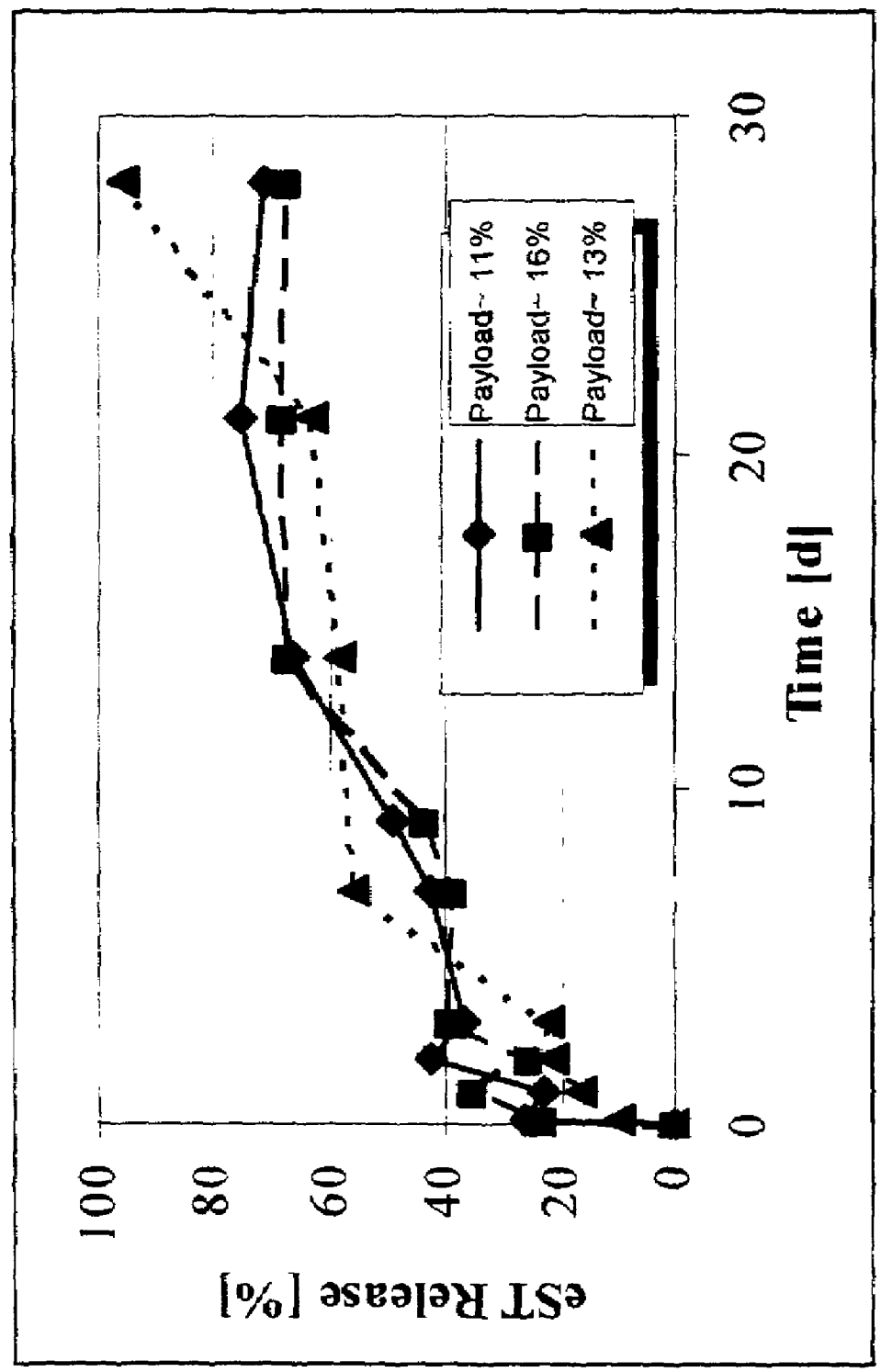
FIG. 9 depicts rate of release from the formulations prepared according to Examples 45–47.

FIG. 9 depicts the in vitro-release (over four weeks) from prepared eST microparticles.

We claim:

1. A process for the production of polymeric microparticles comprising dissolving a polymer in a halogen-free solvent, said solvent being at least partially water-miscible, to form a polymer solution, said solvent being selected from acetone, ethanol, alkyl acetates, alkyl formates, triacetin, triethyl citrate, C1–C4-alkyl lactates, methyl ethyl ketone, methyl isobutyl ketone, tetrahydrofuran, dimethyl sulfoxide, 1-methyl-2-pyrrolidone, 3-methyl-1-butanol, acetonitrile, PEG 100, PEG 400, N-methyl-pyrrolidone, glycofurol, diethylcarbonate and 2-methyl-1-propanol and mixtures thereof; adding a hydrophilic active agent to the polymer solution to form a drug phase contained in a vessel; adding a predetermined amount of an aqueous surfactant phase, wherein the volume fraction of the surfactant phase is at least 0.60, to the vessel containing the drug phase with mixing, wherein $\delta_{polymer\ solvent} - \delta_{aqueous\ phase} < 0$, said predetermined amount being sufficient to provide that the surfactant phase becomes the continuous phase and extraction medium in order to extract an amount of said solvent from said drug phase such that a suspension of microparticles is produced upon addition of the surfactant phase to the drug phase without the formation of an intermediate W/O/W double emulsion and without requiring removal of solvent from the vessel, wherein a suspension of the polymeric microcapsules is formed within one minute of mixing the surfactant phase with the drug phase.

2. A process according to claim 1 further comprising removing the solvent.

3. A process according to claim 2 wherein the solvent is removed by washing, filtration, vacuum, or evaporation.

4. A process according to claim 1 wherein the solvent has a water solubility of 1.5–40 wt % in water.

5. A process according to claim 4 wherein the solvent solubility is at least 5 wt % in water.

6. A process according to claim 5 wherein the solvent solubility is at least 10 wt % in water.

7. A process according to claim 1 wherein the volume fraction of the surfactant phase is 0.65–0.75.

8. A process according to claim 1 wherein the volume ratio of polymer phase: surfactant phase is within the range 1:2–1:30.

9. A process according to claim 8 wherein the ratio is 1:2–1:20.

10. A process according to claim 1 further comprising adding a water-miscible co-solvent to the surfactant phase wherein said polymer solvent is soluble in said co-solvent and said polymer is not soluble in said co-solvent.

11. A process according to claim 10 wherein said co-solvent is selected from the group consisting of alcohols, polyethylene glycol, and ethers.

12. A process according to claim 11 wherein the co-solvent is selected from the group consisting of ethanol, methanol, isopropyl alcohol, and polyethylene glycol.

13. A process according to claim 1 further comprising adding a buffer to the drug phase.

14. A process according to claim 1 further comprising adding a buffer to the surfactant phase.

15. A process according to claim 14 wherein the polymer is not soluble in the surfactant phase.

16. A process according to claim 1 wherein the microparticles comprise microcapsules.

17. A process according to claim 1 wherein the microparticles comprise microsponges.

18. A process according to claim 1 wherein the microparticles comprise microspheres.

19. A process according to claim 1 further comprising adding a viscosity modifier to the aqueous surfactant phase.

20. A process according to claim 19 comprising 5–50 wt % of the viscosity modifier.

21. A process according to claim 20 wherein the viscosity modifier is selected from the group consisting of glycerol, hyaluronic acid, cellulose polymers, chitosane, or polyethylene glycol.

22. The process according to claim 13, wherein the buffered solution is selected from the group consisting of a phosphate buffer solution, a citrate buffer solution and a tris(hydroxymethyl)aminomethane solution.

23. A process according to claim 1 wherein the polymer is selected from the group consisting of polyamides, polyanhydrides, polyesters, polyorthoesters, polyacetates, polylactones, and polyorthocarbonates.

24. A process according to claim 23 wherein the polymer is selected from the group consisting of polyesters of $\alpha$-, $\beta$- and $\gamma$-hydroxycarboxylic acids, or block copolymers of polyesters of $\alpha$-, $\beta$- and $\gamma$-hydroxycarboxylic acids and linear or star poly(ethylene glycols).

25. A process according to claim 24 wherein the polymer comprises a poly lactide co-glycolide polymer.

26. A process according to claim 1 wherein the partially water-miscible solvent is selected from the group consisting of acetone, ethanol, alkyl acetates, alkyl formates, triacetin, triethyl citrate, and alkyl lactates and mixtures thereof.

27. A process according to claim 26 wherein the solvent is selected from the group consisting of ethanol, acetone, methyl acetate, ethyl acetate, propyl acetate, isopropyl acetate, butyl acetate, methyl formate, ethyl formate, propyl formate, isopropyl formate, butyl formate, triacetin, methyl lactate, ethyl lactate and mixtures thereof.

28. A process according to claim 1 wherein the surfactant is a non-ionic surfactant.

* * * * *